US009073977B2

(12) United States Patent
Zuckermann et al.

(10) Patent No.: US 9,073,977 B2
(45) Date of Patent: Jul. 7, 2015

(54) BIOMIMETIC PEPTOID POLYMERS

(75) Inventors: Ronald N. Zuckermann, El Cerrito, CA (US); Tammy K. Chu, San Leandro, CA (US); Ki Tae Nam, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 397 days.

(21) Appl. No.: 13/022,548

(22) Filed: Feb. 7, 2011

(65) Prior Publication Data

US 2012/0046443 A1 Feb. 23, 2012

Related U.S. Application Data

(63) Continuation-in-part of application No. PCT/US2009/053037, filed on Aug. 6, 2009.

(60) Provisional application No. 61/086,773, filed on Aug. 6, 2008.

(51) Int. Cl.
| | | |
|---|---|---|
| C40B 40/10 | (2006.01) |
| C07K 7/06 | (2006.01) |
| C07K 7/08 | (2006.01) |
| C07K 14/00 | (2006.01) |
| C07K 1/13 | (2006.01) |

(52) U.S. Cl.
CPC .............. C07K 14/001 (2013.01); *C07K 7/08* (2013.01); *C07K 7/06* (2013.01); *C07K 1/13* (2013.01)

(58) Field of Classification Search
CPC ....... C08G 69/10; C07K 14/001; C40B 40/10

USPC .............. 506/15, 18; 530/324, 325, 326, 327, 530/328, 329, 330; 930/20, 30
See application file for complete search history.

(56) References Cited

U.S. PATENT DOCUMENTS

| | | | |
|---|---|---|---|
| 5,877,278 A | 3/1999 | Zuckermann et al. | |
| 6,677,445 B1 | 1/2004 | Innis et al. | |
| 6,783,929 B1 | 8/2004 | Zuckermann et al. | |
| 6,887,845 B2 | 5/2005 | Barron et al. | |
| 7,026,166 B2 | 4/2006 | Suich et al. | |
| 7,030,216 B2 | 4/2006 | Horn et al. | |
| 7,153,682 B2 | 12/2006 | Charych et al. | |
| 7,408,023 B2 | 8/2008 | Horn et al. | |
| 7,422,861 B2 | 9/2008 | Zuckermann et al. | |
| 7,834,144 B2 * | 11/2010 | Peretz et al. | .................. 530/328 |
| 8,114,830 B2 | 2/2012 | Barron et al. | |

(Continued)

OTHER PUBLICATIONS

PCT/US09/53037 International Search Report.

(Continued)

*Primary Examiner* — Samuel Woolwine
*Assistant Examiner* — Kaijiang Zhang
(74) *Attorney, Agent, or Firm* — Robin C. Chang; Lawrence Berkeley National Laboratory

(57) ABSTRACT

The present invention provides for novel peptoid oligomers that are capable of self-assembling into two-dimensional sheet structures. The peptoid oligomers can have alternately hydrophilic or polar side-chains and hydrophobic or apolar side-chains. The peptoid oligomers, and the two-dimensional sheet structures, can be applied to biological applications where the peptoid plays a role as a biological scaffold or building block. Also, the two-dimensional sheet structures of the present invention can be used as two-dimensional nanostructures in device applications.

17 Claims, 14 Drawing Sheets

(56) References Cited

U.S. PATENT DOCUMENTS

| | | | |
|---|---|---|---|
| 8,673,842 | B2 | 3/2014 | Barron et al. |
| 8,772,255 | B2 | 7/2014 | Burkoth et al. |
| 2004/0249122 | A1 | 12/2004 | Blazyk |
| 2007/0087972 | A1* | 4/2007 | Peretz et al. ............ 514/16 |
| 2007/0116646 | A1* | 5/2007 | Klaveness et al. ......... 424/9.6 |

OTHER PUBLICATIONS

PCT/US09/53037 Written Opinion of the International Searching Authority.
PCT/US09/53037 International Preliminary Report on Patentability.
Simon et al., Peptoids—a Modular Approach to Drug Discovery, Proc. Natl. Acad. Sci. USA 1992, 89 (20), 9367-9371.
Zuckermann et al., Efficient Method for the Preparation of Peptoids [Oligo(N-Substituted Glycines)] by Submonomer Solid-Phase Synthesis. Journal of the American Chemical Society 1992, 114 (26), 10646-10647.
Armand, et al. NMR determination of the major solution conformation of a peptoid pentamer with chiral side chains. Proceedings of the National Academy of Sciences of the United States of America 1998, 95, 4309-4314.
Kirshenbaum et al., Sequence-specific polypeptoids: A diverse family of heteropolymers with stable secondary structure, Proceedings of the National Academy of Sciences of the United States of America 1998, 95, 4303-4308.
Wu et al., "Peptoid oligomers with a-chiral, aromatic side chains: sequence requirements for the formation of stable peptoid helices," J. Am. Chem. Soc. 2001, 123: 6778-6784.
Wu et al., "Peptoid oligomers with a-chiral, aromatic side chains: effects of chain length on secondary structure," J. Am. Chem. Soc. 2001, 123: 2958-2963.
Sanbom et al., "Extreme stability of helices formed by water-soluble poly-N-substituted glycines (polypeptoids) with a-chiral side chains," Biopolymers 2002, 63: 12-20.
Lee, et al. Folding a Nonbiological Polymer into a Compact Multihelical Structure. Journal of the American Chemical Society 2005, 127, 10999-11009.
Lee, et al., Biomimetic Nanostructures: Creating a High-Affinity Zinc-Binding Site in a Folded Nonbiological Polymer. Journal of the American Chemical Society 2005, 127, 10999-11009.
Figliozzi, et al. Synthesis of N-(substituted)glycine Peptoid Libraries. Methods in Enzymology 1996, 267, 437-447.
Xiong et al., Periodicity of polar and nonpolar amino acids is the major determinant of secondary structure in self-assembling oligomeric peptides. Proceedings of the National Academy of Sciences of the United States of America 1995, 92, 6349-6353.
Panchuk-Voloshina et al., Alexa Dyes, a series of new fluorescent dyes that yield exceptionally bright, photostable conjugates, J. Histochem. Cytochem. 47(9): 1179-1188, 1999.
Wender et al., The design, synthesis, and evaluation of molecules that enable or enhance cellular uptake: Peptoid molecular transporters. Proc. Natl. Acad. Sci. USA, 97(24):13003-13008, 2000.

* cited by examiner

A

B

US 9,073,977 B2

BIOMIMETIC PEPTOID POLYMERS

CROSS-REFERENCE TO RELATED APPLICATIONS

This application claims priority to PCT International Patent Application No. PCT/US09/53037, filed Aug. 6, 2009, which claims priority to U.S. Provisional Patent Application Ser. No. 61/086,773, filed on Aug. 6, 2008; which are hereby incorporated by reference.

STATEMENT OF GOVERNMENTAL SUPPORT

The invention described and claimed herein was made in part utilizing funds supplied by the U.S. Department of Energy under Contract No. DE-AC02-05CH11231. The government has certain rights in this invention.

FIELD OF THE INVENTION

This invention relates generally to peptoids.

BACKGROUND OF THE INVENTION

Biological self assembly and biomolecular recognition continue to inspire novel approaches for the fabrication of bioanalytical, electrical and optical devices, via the organization of building blocks into hierarchical structures (Mann, S., *Biomimetic materials chemistry*. VCH: New York, 1996; p xvi, 383 p.; Weiner, S.; Addadi, L.; Wagner, H. D., Materials design in biology. *Materials Science & Engineering C-Biomimetic and Supramolecular Systems* 2000, 11 (1), 1-8). Self-assembling peptide and protein systems have been used to make wires, fibers, tubes, vesicles and other structures that are highly ordered on the nanometer scale (Zhang, S. G., Fabrication of novel biomaterials through molecular self-assembly. *Nat Biotechnol* 2003, 21 (10), 1171-1178; Hartgerink, J. D.; Beniash, E.; Stupp, S. I., Self-assembly and mineralization of peptide-amphiphile nanofibers. *Science* 2001, 294 (5547), 1684-1688; Aggeli, A.; Nyrkova, I. A.; Bell, M.; Harding, R.; Carrick, L.; McLeish, T. C. B.; Semenov, A. N.; Boden, N., Hierarchical self-assembly of chiral rod-like molecules as a model for peptide beta-sheet tapes, ribbons, fibrils, and fibers. *Proc. Natl. Acad. Sci. USA* 2001, 98 (21), 11857-11862). However, the potential of these systems for assembling devices is limited in part by difficulties in controlling the geometry of the self-assembling components. A significant prerequisite for the fabrication of useful nanodevices in electronic and biomedical applications is the construction of well-ordered two-dimensional structures, because most device architectures are based on the stacking of two-dimensional components. Sheet-like two-dimensional materials are a fundamentally important geometry for device construction, and yet there are relatively few ways to prepare such materials by self-assembly. Their use includes components of bioanalytical devices, electrochemical devices (such as batteries, fuel cells and supercapacitors), membranes for filtration and separation, surface coatings with chemically defined surfaces and biosensors.

Currently, two-dimensional assembly has been achieved at the interface of liquid-liquid, liquid-solid and liquid-air which acts as a template. Two popular methods are self assembled monolayers (SAM) and Langmuir-Blodgett monolayers (LBM) (Ulman, A., Formation and structure of self-assembled monolayers. *Chemical Reviews* 1996, 96 (4), 1533-1554). The self-assembled monolayers are based on the covalent bonding between the assembling molecules and a surface template (Bain, C. D.; Whitesides, G. M., Molecular-Level Control over Surface Order in Self-Assembled Monolayer Films of Thiols on Gold. *Science* 1988, 240 (4848), 62-63). The template is an absolute requirement, as the monolayers are chemically bonded to the surface. In the Langmuir-Blodgett monolayers, the hydrophobic molecules are segregated and spread to form a monolayer at the air-water interface. The assembled species can be transferred to the other processable solid surfaces, but this is a delicate process as the films are often quite fragile, and the process is not scaleable.

Chemical synthesis also represents another research direction to fabricate two-dimensional nanostructures. A variety of inorganic materials have been fabricated into planar structures of various sizes using solution-based methods (Dikin, D. A.; Stankovich, S.; Zimney, E. J.; Piner, R. D.; Dommett, G. H. B.; Evmenenko, G.; Nguyen, S. T.; Ruoff, R. S., Preparation and characterization of graphene oxide paper. *Nature* 2007, 448 (7152), 457-460; Viculis, L. M.; Mack, J. J.; Kaner, R. B., A chemical route to carbon nanoscrolls. *Science* 2003, 299 (5611), 1361-1361; Tang, Z. Y.; Zhang, Z. L.; Wang, Y.; Glotzer, S. C.; Kotov, N. A., Self-assembly of CdTe nanocrystals into free-floating sheets. *Science* 2006, 314 (5797), 274-278). In these cases, electrostatic interactions and anisotropic hydrophobic attraction were used to drive the assembly of nanocrystals into sheet structures. However, the range of composition is limited to certain kinds of oxide materials which have the layered structure in one direction. Additionally, it is hard to generalize the strategy and can be rarely extended to other sheets with different compositions.

Biomolecules such as proteins (Xu, G. F.; Wang, W. X.; Groves, J. T.; Hecht, M. H., Self-assembled monolayers from a designed combinatorial library of de novo beta-sheet proteins. *Proc. Natl. Acad. Sci. USA* 2001, 98 (7), 3652-3657), peptides (Rapaport, H.; Kjaer, K.; Jensen, T. R.; Leiserowitz, L.; Tirrell, D. A., Two-dimensional order in beta-sheet peptide monolayers. *Journal of the American Chemical Society* 2000, 122 (50), 12523-12529; Zhang, S. G.; Holmes, T.; Lockshin, C.; Rich, A., Spontaneous Assembly of a Self-Complementary Oligopeptide to Form a Stable Macroscopic Membrane. *Proc. Natl. Acad. Sci. USA* 1993, 90 (8), 3334-3338; Vauthey, S.; Santoso, S.; Gong, H. Y.; Watson, N.; Zhang, S. G., Molecular self-assembly of surfactant-like peptides to form nanotubes and nanovesicles. *Proc. Natl. Acad. Sci. USA* 2002, 99 (8), 5355-5360; Aggeli, A.; Bell, M.; Boden, N.; Keen, J. N.; Knowles, P. F.; McLeish, T. C. B.; Pitkeathly, M.; Radford, S. E., Responsive gels formed by the spontaneous self-assembly of peptides into polymeric beta-sheet tapes. *Nature* 1997, 386 (6622), 259-262), lipids (Groves, J. T.; Ulman, N.; Boxer, S. G., Micropatterning fluid lipid bilayers on solid supports. *Science* 1997, 275 (5300), 651-653), and DNA (Winfree, E.; Liu, F. R.; Wenzler, L. A.; Seeman, N. C., Design and self-assembly of two-dimensional DNA crystals. *Nature* 1998, 394 (6693), 539-544) have also been demonstrated to assemble into two-dimensional structures. These materials may suffer many disadvantages as a material to fabricate into devices. They are typically not stable for long periods, or at extremes of temperature, pH, solvents or other non-physiological conditions. They can be difficult to produce on a large scale. They can rarely from stable, flat two-dimensional sheet structures over long distance scales. This hinders innovation and inhibits realization of commercial applications of biological self-assembly. One challenge with achieving highly ordered self assembled peptide-based materials is that the high amount of hydrogen bonding can lead to kinetically trapped structures, making it difficult to form a thermodynamically stable uniform structure.

SUMMARY OF THE INVENTION

The present invention provides for a peptoid oligomer having the structure:

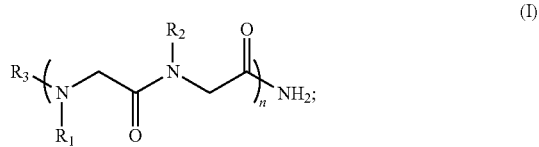

(I)

wherein $R_1$ is a hydrophilic or polar side-chain and $R_2$ is a hydrophobic or apolar side-chain, or $R_2$ is a hydrophilic or polar side-chain and $R_1$ is a hydrophobic or apolar side-chain, $R_3$ is H or a capping group, and n is an integer equal to or greater than 2. The structure defined within the brackets is a monomer subunit. The monomer subunits can be identical or distinct from each other.

The present invention provides for a peptoid oligomer having the structure:

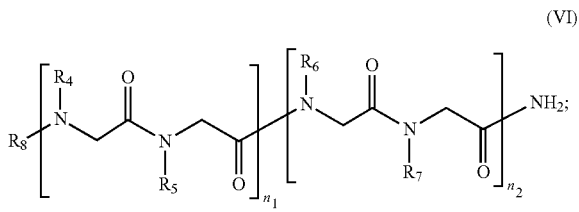

(VI)

wherein (a) $R_4$ is a hydrophilic or polar side-chain and $R_5$ is a hydrophobic or apolar side-chain, and $R_6$ is a negative-charged hydrophilic or polar hydrophilic side-chain and $R_7$ is a hydrophobic or apolar side-chain, wherein $R_4$ and $R_6$ are positive-charged or basic and negative-charged or acidic side-chains, respectively, or vice versa, or (b) $R_5$ is a hydrophilic or polar side-chain and $R_4$ is a hydrophobic or apolar side-chain, and $R_7$ is a negative-charged hydrophilic or polar hydrophilic side-chain and $R_6$ is a hydrophobic or apolar side-chain, wherein $R_4$ and $R_6$ are positive-charged or basic and negative-charged or acidic side-chains, respectively, or vice versa; $R_8$ is H or a capping group; $n_1$ and $n_2$ are an integer equal to or greater than 2; and, $n_1$ and $n_2$ are about equal to each other. The structures defined within the each bracket is a monomer subunit. The monomer subunits can be identical or distinct from each other.

The peptoid oligomer of the present invention is capable of self-assembling with one or more identical or different peptoid oligomer into a dimer or 2-dimension sheet.

The present invention provides for a population of the peptoid oligomers of the present invention.

The present invention also provides for a two-dimensional sheet comprising a peptoid oligomer defined herein assembled into a two-dimensional sheet structure. The two-dimensional sheet can be formed by self-assembling by its constituent peptoid oligomers.

The present invention provides for a method for synthesizing a two-dimensional sheet comprising: (a) providing one or more population of peptoid oligomers of the present invention; and (b) incubating the population in a condition suitable for the population to self-assemble into a two-dimensional sheet; whereby the two-dimensional sheet is synthesized.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
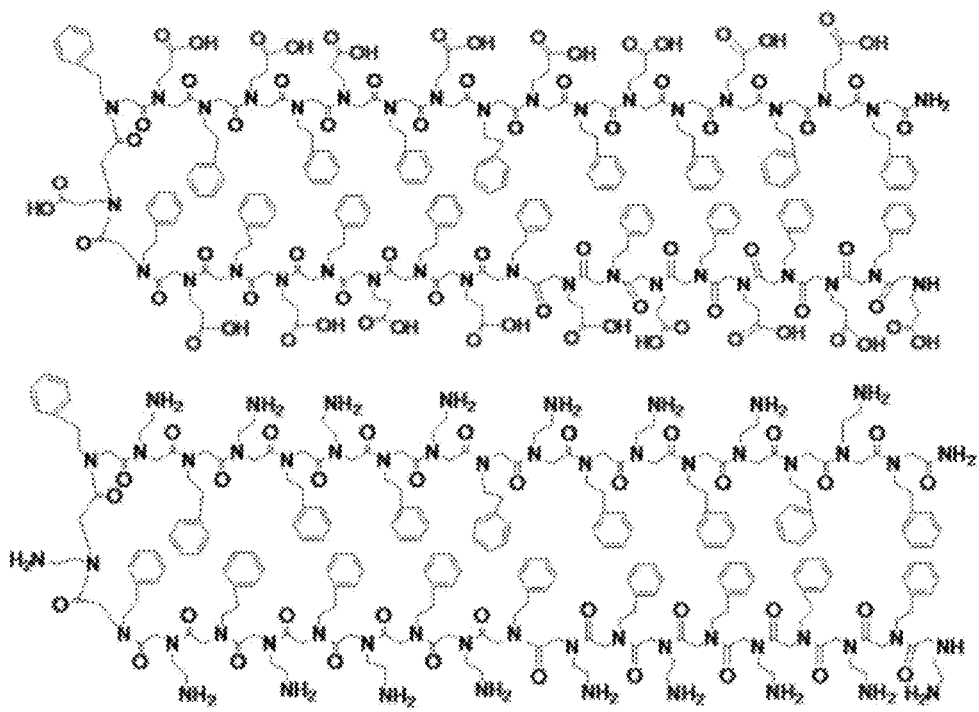
FIG. 1 shows a chemical structure of sheet-forming peptoid pair. These two compounds form sheets when mixed together in equal amounts in aqueous solution.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peptoid oligomer" includes a plurality of such peptoid oligomers, and so forth.

In this specification and in the claims that follow, reference will be made to a number of terms that shall be defined to have the following meanings:

These and other objects, advantages, and features of the invention will become apparent to those persons skilled in the art upon reading the details of the invention as more fully described below.

The present invention provides for a peptoid oligomer having the structure:

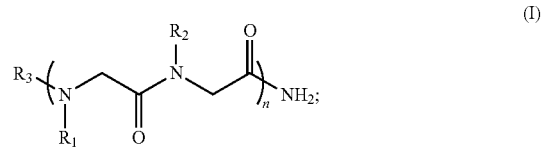

(I)

wherein $R_1$ is a hydrophilic or polar side-chain and $R_2$ is a hydrophobic or apolar side-chain, or $R_2$ is a hydrophilic or polar side-chain and $R_1$ is a hydrophobic or apolar side-chain, $R_3$ is H or a capping group, and n is an integer equal to or greater than 2. The structure defined within the brackets is a monomer subunit. The monomer subunits can be identical or distinct from each other.

For example, if $N_1$, $N_2$, $N_3$, $N_4$, $N_5$, and $N_6$ are distinct monomer subunits, possible peptoid oligomers include, but are not limited to:

$$R_3—N_1—N_1—N_1—N_1—N_1—N_1—\ldots—NH_2 \quad (II)$$

$$R_3—N_1—N_2—N_1—N_2—N_1—N_2—\ldots—NH_2 \quad (III)$$

$$R_3—N_1—N_2—N_3—N_1—N_2—N_3—\ldots—NH_2 \quad (IV)$$

$$R_3—N_1—N_2—N_3—N_4—N_5—N_6—\ldots—NH_2 \quad (V)$$

The peptoid oligomer can have one or more repeating monomer subunit. For example, structure (II) has a single repeating monomer subunit, while structures (III) and (IV) have two and three repeating monomer subunits, respectively. Alternately, the peptoid oligomer can have random, or purposefully all different, monomer subunits as in structure (V).

The present invention provides for a peptoid oligomer having the structure:

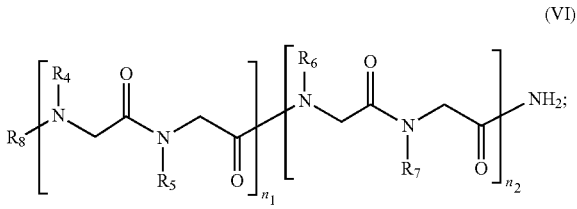

(VI)

wherein (a) $R_4$ is a hydrophilic or polar side-chain and $R_5$ is a hydrophobic or apolar side-chain, and $R_6$ is a negative-charged hydrophilic or polar hydrophilic side-chain and $R_7$ is a hydrophobic or apolar side-chain, wherein $R_4$ and $R_6$ are positive-charged or basic and negative-charged or acidic side-chains, respectively, or vice versa, or (b) $R_5$ is a hydrophilic or polar side-chain and $R_4$ is a hydrophobic or apolar side-chain, and $R_7$ is a negative-charged hydrophilic or polar hydrophilic side-chain and $R_6$ is a hydrophobic or apolar side-chain, wherein $R_4$ and $R_6$ are positive-charged or basic and negative-charged or acidic side-chains, respectively, or vice versa; $R_8$ is H or a capping group; $n_1$ and $n_2$ are an integer equal to or greater than 2; and, $n_1$ and $n_2$ are about equal to each other. The structures defined within the each bracket is a monomer subunit. The monomer subunits can be identical or distinct from each other. In some embodiments of the invention, $n_1$ and $n_2$ are equal to or more than about 2, 3, 4, 5, 6, 7, 8, or 9. In some embodiments of the invention, $n_1$ and $n_2$ are equal to or less than about 10, 20, 30, 50; or 100. In some embodiments of the invention, $n_1$ and $n_2$ are an integer ranging from equal to or more than about 2, 3, 4, 5, 6, 7, 8, or 9 to equal to or less than about 10, 20, 30, 50, or 100. $n_1$ and $n_2$ may differ in value, such as 1 or 2, as long as the peptoid oligo is still capable of self-assembling with one or more identical peptoid oligo into a dimer or 2-dimension sheet.

The peptoid oligomer of the present invention is capable of self-assembling with one or more identical or different peptoid oligomer into a dimer or 2-dimension sheet.

The present invention provides for a population of the peptoid oligomers of the present invention. The peptoid oligomers within the population can comprise (a) identical or different numbers of monomer subunits, (b) monomer subunits of identical side-chains or different side-chains, and/or (c) identical or different $R_3$. In some embodiments of the invention, the population can comprise one or more sub-populations of peptoid oligomers, wherein each sub-population of peptoid oligomers comprises identical peptoid oligomers, except wherein n can be an identical or different number within each sub-population.

The side-chain is a group attached to the polyamide backbone of a compound of chemical structure. Side-chains may be $R_a$, —$OR_a$, —$NR_aR_b$, —$SO_{1,2,3,4}R_a$, —$C(O)R_a$, —$C(O)OR_a$, —$OC(O)R_a$, —$OC(O)OR_a$, —$NR_bC(O)R_a$, —$C(O)NR_aR_b$, —$OC(O)NR_aR_b$, —$NR_c C(O)NR_aR_b$, —$NR_bC(O)OR_a$, —$R_a$—O—$R_b$, —$R_a$—$NR_bR_c$, —$SO_3$, —$SO_4$, —$SO_2NH$—$R_a$, —$R_a$—S—$R_b$, —$R_a$—S(O)—$R_b$, —$R_a$—$S(O)_2$—$R_b$, —$OR_a$—O—$R_b$, —$NR_aR_b$—O—$R_c$, —$SO_{1,2,3,4}R_a$—O—$R_b$, —$C(O)R_a$—O—$R_b$, —$C(O)OR_a$—O—$R_b$, —$OC(O)R_a$—O—$R_b$, —$OC(O)OR_a$—O—$R_b$, —$NR_bC(O)R_a$—O—$R_c$, —$C(O)NR_aR_b$—O—$R_c$, —$OC(O)NR_aR_b$—O—$R_c$, —$NR_cC(O)NR_aR_b$—O—$R_d$, —$NR_bC(O)OR_a$—O—$R_c$, —$OR_a$—S—$R_b$, —$NR_aR_b$—S—$R_c$, —$SO_{1,2,3,4}R_a$—S—$R_b$, —$C(O)R_a$—S—$R_b$, —$C(O)OR_a$—S—$R_b$, —$OC(O)OR_a$—S—$R_b$, —$OC(O)OR_a$—S—$R_b$, —$NR_bC(O)R_a$—S—$R_c$, —$C(O)NR_aR_b$—S—$R_c$, —$OC(O)NR_aR_b$—S—$R_c$, —$NR_cC(O)NR_aR_b$—S—$R_d$, —$NR_bC(O)OR_a$—S—$R_c$, —$OR_a$—$NR_bR_d$, —$NR_aR_b$—$NR_cR_d$, —$SO_{1,2,3,4}R_a$—$NR_bR_d$, —$C(O)R_a$—$NR_bR_d$, —$C(O)OR_a$—$NR_bR_d$, —$OC(O)R_a$—N—$R_bR_d$, —$OC(O)OR_a$—$NR_bR_d$, —$NR_bC(O)R_a$—$NR_cR_d$, —$C(O)NR_aR_b$—$NR_cR_d$, —$OC(O)NR_aR_b$—$NR_cR_d$, —$NR_cC(O)NR_aR_b$—$NHR_b$, —$NR_bC(O)OR_a$—$NR_cR_d$, —$PO_3$, —$PO_4$, —$PO_2$—$R_a$, —$R_a$—$PO_3$, —$R_a$—$PO_4$, —$R_a$—$PO_2$—$R_b$; wherein $R_a$, $R_b$, $R_c$, and $R_d$ are each independently 1-1, alkyl, alkenyl, alkynyl, aryl, aralkyl, aralkenyl, or aralkynyl; wherein $R_a$, $R_b$, $R_c$ and $R_d$ can each be independently substituted with 0-6 halo, $NO_2$, —OH, lower alkyl, —SH, —$SO_3$, —$NH_2$, —C(O)OH, lower acyl, lower acyloxy, lower alkylamino, lower dialkylamino, trihalomethyl, —CN, lower alkylthio, lower alkylsufinyl, or lower alkylsulfonyl; wherein the number of carbon atoms in the longest carbon chain of $R_a$, $R_b$, $R_c$ and $R_d$ is equal to or less than eighteen; wherein one hydrophilic or polar side-chain out of a plurality of hydrophilic or polar side-chains within each oligomer (such one out of 10 or more, or 100 or more) may or may not comprise a functional group, such as a dye or a point of attachment to link to another molecule of interest; and with the proviso than when the side-chain is $R_a$, $R_a$ comprises at least two carbon atoms. A functional group that is defined as "lower" means the functional group comprises one or more, and six or less, carbons.

The dye can be any suitable dye molecule capable of attaching, such as with a covalent bond, to a side chain. Suitable dyes include, but are limited to, Alexa Fluor® dyes, such as Alexa Fluor® 405, Alexa Fluor® 305, Alexa Fluor® 500, Alexa Fluor® 488, Alexa Fluor® 430, Alexa Fluor® 514, Alexa Fluor® 532 Alexa Fluor® 555, Alexa Fluor® 546, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, and Alexa Fluor® 750 dyes, and in maleimide form thereof. The Alexa Fluor® dyes are commercially available from Life Technologies Corp., Carlsbad, Calif.

The hydrophilic or polar side-chain is a side-chain that comprises one or more —$OCH_3$, diol, triol, sugar, —$PO_3$, —$PO_4$, —$PO_2$—$R_b$, —$SO_3$, —$SO_4$, or —$SO_2NH$—$R_b$, one or more ionic charge, is capable of hydrogen-bonding, and/or has a net log P value that is less than 0. In some embodiments, the hydrophilic side-chain is —$R_a$—C(O)OH or —$R_a$—$NH_2$. In some embodiments, the hydrophilic side-chain is —$R_a$—X, wherein X is —OH, —C(O)H, —C(O)OH, —SH, —$NH_2$, or —C(O)—$NH_2$, and wherein $R_a$ is defined herein. In some embodiments, $R_a$ is —$(CH_2)_m$—, wherein m is equal to or more than 2, and equal to or less than 18. In some embodiments, m is equal to or more than 2, and equal to or less than 15. In some embodiments of the invention, the polar side-chain is a carboxylated alkyl, such as —$CH_2$—$CH_2$—COOH, or an aminated alkyl, such as —$CH_2$—$CH_2$—$NH_2$.

The hydrophobic or apolar side-chain is a side-chain that does not comprises an ionic charge, is not capable of hydrogen-bonding, and/or has a net log P value that is equal to or more than 0.5. In some embodiments, the hydrophobic side-chain has a net log P value that is equal to or more than 1 or 2. In some embodiments, the hydrophilic side-chain is —$R_a$—Y, wherein Y is a hydrophobic functional group and $R_a$ is defined herein. Examples of hydrophobic functional groups include, but are not limited to, any lower alkyl, a benzene, and a benzene substituted with any lower alkyl. In some embodiments, $R_a$ is —$(CH_2)_p$—, wherein p is equal to or more than 2, and equal to or less than 18. In some embodiments, p is equal to or more than 2, and equal to or less than 15. In some embodiments of the invention, the apolar side-chain is an aralkyl, such as —$CH_2$—$CH_2$—$C_6H_5$.

Quantitatively, polar group and apolar group can be determined by measure of partition coefficient P. Partition coefficient is the logarithm ratio of concentrations of a compound in water and octanol (Leo A, Hansch C, and Elkins D (1971). "Partition coefficients and their uses". *Chem Rev* 71 (6): 525-616):

$$\log P = \log([\text{Solute}]_{octanol}/[\text{Solute}]_{water}).$$

The capping group can be $R_a$ as defined herein. In some embodiments, $R_a$ comprises equal to or less than 5 carbon atoms. The capping group does not prevent the peptoid oligomers from self-assembling into a two-dimensional sheet.

The peptoid oligomers include homopolymers, copolymers and interpolymers of any length. Oligomers may be comprised of two or more monomer subunits, wherein each monomer subunit comprises a hydrophilic side-chain and a hydrophobic side-chain. In some embodiments, the oligomer comprises 10 or more monomer subunits. In some embodiments, the oligomer comprises 20 or more monomer subunits. In some embodiments, the oligomer comprises 30 or more monomer subunits. In some embodiments, the oligomer comprises 36 or more monomer subunits. In some embodiments, the oligomer comprises 2-100 monomer subunits. The upper limit of the number of monomer subunits can be 100, 500, 1000, or 5000.

The present invention also provides for a two-dimensional sheet comprising a peptoid oligomer defined herein assembled into a two-dimensional sheet structure. The two-dimensional sheet can be formed by self-assembling by its constituent peptoid oligomers. A two-dimensional sheet that comprises a dye or a point of attachment to link to another molecule of interest is a functionalized sheet.

The present invention provides for a new system for the construction of two-dimensional sheet structures using a class of biomimetic polymer called peptoids. Peptoids are a class of non-natural polymer based on oligo-N-substituted glycines, designed to mimic peptides and proteins (Simon, R. J.; Kania, R. S.; Zuckermann, R. N.; Huebner, V. D.; Jewell, D. A.; Banville, S.; Ng, S.; Wang, L.; Rosenberg, S.; Marlowe, C. K.; Spellmeyer, D. C.; Tan, R. Y.; Frankel, A. D.; Santi, D. V.; Cohen, F. E.; Bartlett, P. A., Peptoids—a Modular Approach to Drug Discovery. *Proc. Nail. Acad. Sci. USA* 1992, 89 (20), 9367-9371; herein incorporated by reference). The peptoid side chains are appended to the amide nitrogen rather than to the alpha carbon as in a peptide. The present invention involves the formation of two-dimensional structures of peptoids, and the use of these materials to drive the assembly or growth of biomolecules and inorganic materials into planar assemblies.

Figure 2:
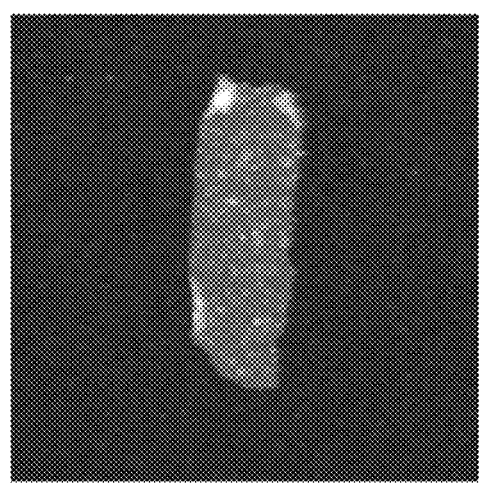
FIG. 2 shows the atomic force microscopy (AFM) image of peptoid based sheet. This image is height mode images (Z range: 40 nm) captured under dry condition with a scan range of 2 μm×2 μm.
Figure 3:
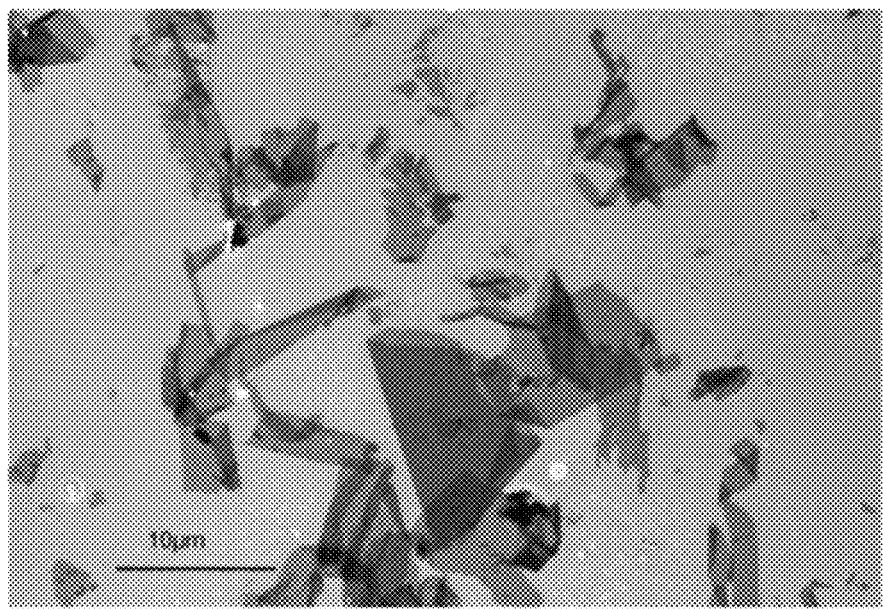
FIG. 3 shows the Scanning Electron Microscopy (SEM) image of peptoid based sheets. Panel A shows a group of peptoid based sheets formed by self-assembling of a population of the peptoid oligomers of the present invention. Panel B shows an about 3 μm×2 μm sheet. The sheet was formed by self-assembling of a population of the peptoid oligomers of the present invention which was mixed at 10 μM and incubated at room temperature (RT) overnight.
Figure 3:
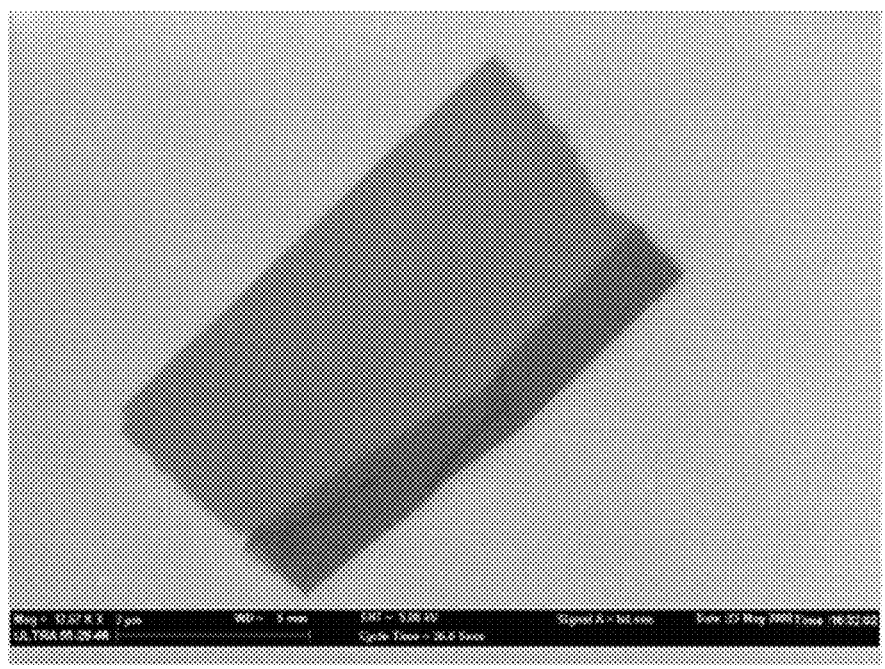

The present invention pertains to compositions and sequences of peptoids that drive two-dimensional self-assembly (for example, see FIGS. 2 and 3). It also includes hybrid molecules or conjugates that possess the peptoid polymer as well as a functional unit(s) attached to the sheet surface or interior. More specifically, the present invention demonstrates that peptoids consisting of alternating polar (P) and apolar (A) residues can be self-assembled into a two-dimensional sheet. The polar side chain needs to be hydrophilic, and the apolar side chain needs to be hydrophobic. The thickness of sheet is in the range of 2-10 nm (i.e. only a few molecules thick) and the size of the planar dimensions can range from nanometer to centimeter or more. A regular repeating peptoid polymer sequence with the alternating $(AP)_n$ motif is capable of assembly into sheets. The number of repeats (n) needs to be a minimum of 2, and the upper limit may only be a limit of synthetic accessibility. The materials can be made by solid-phase synthesis (in which case the accessible lengths are <50 repeats) or by solution polymerization of smaller subunits to generate higher molecular weight materials.

The process is not only limited to the spontaneous assembly of a single peptoid with itself, but it also include the mixing of multiple peptoids with different sequences to form multi-component assemblies. A specific example demonstrated here is the self-assembly of two complementary-charged peptoids in aqueous solution. These sequences each have the $(AX)_n$ motif, where one strand has cationic residues in the "X" position, and the other strand has an anionic residue for the "X" positions. The utilization of the hydrophobic and the electrostatic interaction, which are ubiquitous in nature, can provide the additional flexibility to control the shape and size of sheets and to achieve the dynamic and responsive assembly depending on environmental factors (e.g. pH, salt, temperature, solvent, etc.) Additionally, because the peptoids are bio-inspired synthetic materials exhibiting potent biological activity, the invention has the advantage to interface with biological systems.

The present invention provides for a method for synthesizing a two-dimensional sheet comprising: (a) providing one or more population of peptoid oligomers of the present invention; and (b) incubating the population in a condition suitable for the population to self-assemble into a two-dimensional sheet; whereby the two-dimensional sheet is synthesized.

The providing step can comprise synthesizing the peptoid oligomers.

In some embodiments of the present invention, the condition suitable for the population to self-assemble comprises a solution at about room temperature. The condition can further comprise standing still or agitating by slow mixing or stirring.

In some embodiments of the present invention, the providing step comprises providing two or more populations, and the incubating step comprises introducing a first population to a second population. In some embodiments, the introducing is performed consistently over a period of 30 minutes or more. The introducing can be by pumping using a syringe or pouring from a container.

Peptoids oligomers of the present invention can be synthesized using the methods taught in U.S. Pat. No. 5,877,278 and Zuckermann, R. N.; Kerr, J. M.; Kent, S. B. H.; Moos, W. H., Efficient Method for the Preparation of Peptoids [Oligo(N-Substituted Glycines)] by Submonomer Solid-Phase Synthesis. *Journal of the American Chemical Society* 1992, 114 (26), 10646-10647 (both of which are herein incorporated by reference).

Peptoid oligomers can be synthesized on an automated robot synthesizer using the solid-phase submonomer method (Zuckermann, 1992). Using this method, the Fmoc group on Rink amide resin (0.57 mmol/g, Novabiochem, San Diego, Calif.) is deprotected with 20% piperidine in DMF before starting the submonomer cycle. Peptoid synthesis on resin can be as follows: a 1.2 M solution of bromoacetic acid in DMF (1.13 mL in DMF, 1.35 mmol for 50 µmol of resin) and 0.93 eq. of N,N'-diisopropylcarbodiimide (DIC) (0.20 ml, 1.25 mmol for 50 µmol of resin) is added to a resin-bound amine and mixed for 20 min at 35° C. during the acylation step of the submonomer cycle. The resin-bound bromide can then be displaced with the amine submonomer by adding a 1.5M solution of the amine (0.85 ml for 50 µmol of resin) in N-methylpyrrolidinone (NMP). This displacement reaction can be carried out a suitable condition, such as for 90 min at 35° C. The crude peptoid products (50 µmol of resin) can be cleaved from the resin with a suitable solvent, such as 95:5 trifluoroacetic acid (TFA)/water (v/v), under suitable conditions, such as for 20 min at room temperature. The cleavage solution can be filtered and evaporated under a stream of inert gas, such as nitrogen, to remove the TFA. The crude peptoid product can then be dissolved in a suitable solvent, such as a mixture of water and acetonitrile, and subjected to further purification, such as reverse-phase HPLC on a Vydac C4 column (10 µm, 22 mm×250 mm). All final products can be analyzed by analytical reverse-phase HPLC (5-95% gradient at 1 mL/min over 50 min at 60° C. with a C4, 5 µm, 50×2 mm column) and Matrix-assisted laser desorption/ionization mass spectrometry. The final peptoid products can be lyophilized, dissolved in a suitable solvent, such as either water or buffer (40 mM sodium phosphate buffer, pH 7.0), and stored at −70° C.

There are many methods for the self-assembly of the two complementary-charged peptoid oligomers, such as (Npe–Nae)$_{18}$ and (Npe–Nce)$_{18}$ 36-mers, in aqueous solution. The charge ratio can be from 1:2 to 4:1.

The first method comprises the direct introduction or addition of a first population of peptoid oligomer to a second population of peptoid oligomer. Each populations can have a concentration of about 0.01 mM of the respective peptoid oligomer. The final volume after introduction or addition can be about 1 mL. The sample is left alone overnight before analysis.

Figure 6:
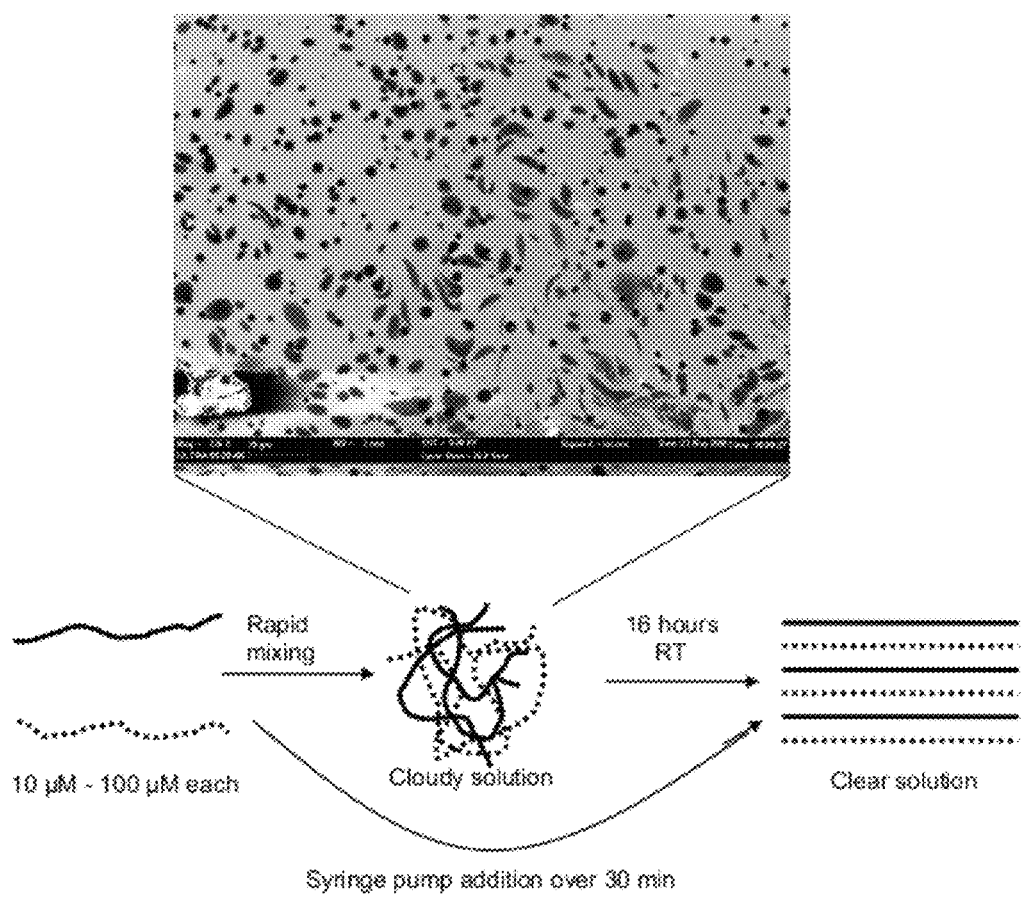
FIG. 6 shows a mixing scheme for self-assembling of the peptoid oligomers of the present invention.

The second method comprises the slow introduction or addition of a first population of peptoid oligomer to a second population of peptoid oligomer. The volume of each can be about 500 µL. The introduction or addition can be via a syringe pump over a course of about 16 hours. The final concentration of both populations of peptoid oligomers can be about 0.01 mM. (See FIG. 6.) Samples can be collected and pipetted onto an oxygen-plasma treated silicon wafer, washed and dried. A scanning electron microscope and an atomic force microscope can be used for the visualization of the sheet structures.

In another method, two or more solutions, each comprising a population of peptoid oligomer, can be mixed in the presence of a denaturing additive, and this solution could then be dialyzed against an aqueous buffer to form the sheets. Suitable denaturants include, but are not limited to, water-miscible organic solvents, high salt, and/or extremes of pH.

In another aspect, the invention includes the two-dimensional assembly of inorganic and organic materials and other biomolecules using the peptoid sheets. After the construction of peptoid-based sheets, technologically important materials can be grown or attached by using the peptoid sheet as a structural template for further applications. Metal ions binding motif or materials specific motif can be incorporated into peptoids sequence. The flexibility, variety of organic, biological or inorganic materials that grow on the surface of the peptoid based sheets, and the low cost of synthesis and assembly of the inventive materials systems will enable many potential technological applications, including, but not limited to, chemical and biological sensors, power devices and catalytic reactive membranes.

All the methods taught herein can be modified by one skilled in the art to suit the specific peptoid oligomer(s) to be synthesized and/or self-assembled.

The present invention provides novel methods to construct two-dimensional assemblies of peptoids of uniform thickness. A wide variety of functional groups can be incorporated into peptoids using the well-developed solid phase synthesis method. This allows the sheets to be functionalized at regular intervals with a variety of moieties. Additionally, peptoids themselves can exhibit potent biological activity. Accordingly, peptoid based self assembly in the invention can take advantage of the synergistic combination of the synthetic polymer and biomimicry. The assembly process and the motif sequence to drive the two dimensional sheets can be applied to biological applications where the peptoid plays a role as a biological scaffold or building block. Extensive tunability of the functionality in peptoids can make it possible to realize multi-component monolayer stacking into higher order structures. Additionally, two-dimensional sheet structures of the present invention can be used as two-dimensional nanostructures in device applications such as bioanalysis, sensors, batteries, supercapacitor, fuel cells, separations, membrane filtration and surface coating layers The invention having been described, the following examples are offered to illustrate the subject invention by way of illustration, not by way of limitation.

EXAMPLE 1

Synthesis of Two Complementary-charged 36-mer Peptoid Oligomers

The following is one example of an embodiment of the present invention. The two complementary-charged peptoids sequences are 36-mers with two-fold periodicity $(AX)_{18}$ that contains alternating polar (X) and non-polar (A) groups. N-(2-phenethyl)glycine (Npe) is used as the non-polar groups while either N-(2-aminoethyl)glycine (Nae) or N-(2-carboxyethyl)glycine (Nce) is used as the polar groups (FIG. 1).

Peptoid oligomers can be synthesized on an automated robot synthesizer using the solid-phase submonomer method (Zuckermann, 1992; herein incorporated by reference). The Fmoc group on Rink amide resin (0.57 mmol/g, Novabiochem, San Diego, Calif.) is deprotected with 20% piperidine in DMF before starting the submonomer cycle. Peptoid synthesis on resin is as follows: a 1.2 M solution of bromoacetic acid in DMF (1.13 mL in DMF, 1.35 mmol for 50 µmol of resin) and 0.93 eq. of N,N'-diisopropylcarbodiimide (DIC) (0.20 ml, 1.25 mmol for 50 µmol of resin) is added to a resin-bound amine and mixed for 20 min at 35° C. during the acylation step of the submonomer cycle. The resin-bound bromide is then displaced with the amine submonomer by adding a 1.5M solution of the amine (0.85 ml for 50 µmol of resin) in N-methylpyrrolidinone (NMP). This displacement reaction is carried out for 90 min at 35° C. The crude peptoid products (50 µmol of resin) are cleaved from the resin with 95:5 trifluoroacetic acid (TFA)/water (v/v) for 20 min at room temperature. The cleavage solution is filtered and evaporated under a stream of nitrogen to remove the TFA. The crude peptoid product is then dissolved in a mixture of water and acetonitrile and subjected to further purification by reverse-phase HPLC on a Vydac C4 column (10 µm, 22 mm×250 mm). All final products are analyzed by analytical reverse-phase HPLC (5-95% gradient at 1 mL/min over 50 min at 60° C. with a C4, 5 µm, 50×2 mm column) and Matrix-assisted laser desorption/ionization mass spectrometry. Final peptoid products are lyophilized, dissolved either in water or buffer (40 mM sodium phosphate buffer, pH 7.0), and stored at −70° C.

There are at least two methods for the self-assembly of the two complementary-charged peptoids, $(Npe-Nae)_{18}$ and $(Npe-Nce)_{18}$ 36-mers in aqueous solution. The first method is direct addition of 0.01 mM of $(Npe-Nce)_{18}$ into 0.01 mM of $(Npe-Nae)_{18}$ with the final volume of 1 mL. The sample is left alone overnight before analysis. The second method is the slow addition of 500 µL of $(Npe-Nce)_{18}$ to 500 µL of $(Npe-Nae)_{18}$ via a syringe pump over a course of 16 hours with the final concentration of 0.01 mM for both $(Npe-Nce)_{18}$ and $(Npe-Nae)_{18}$. (See FIG. 6.) Samples are collected and pipetted onto an oxygen-plasma treated silicon wafer, washed and dried. A scanning electron microscope and an atomic force microscope are used for the visualization of the sheet structures.

EXAMPLE 2

Figure 7:
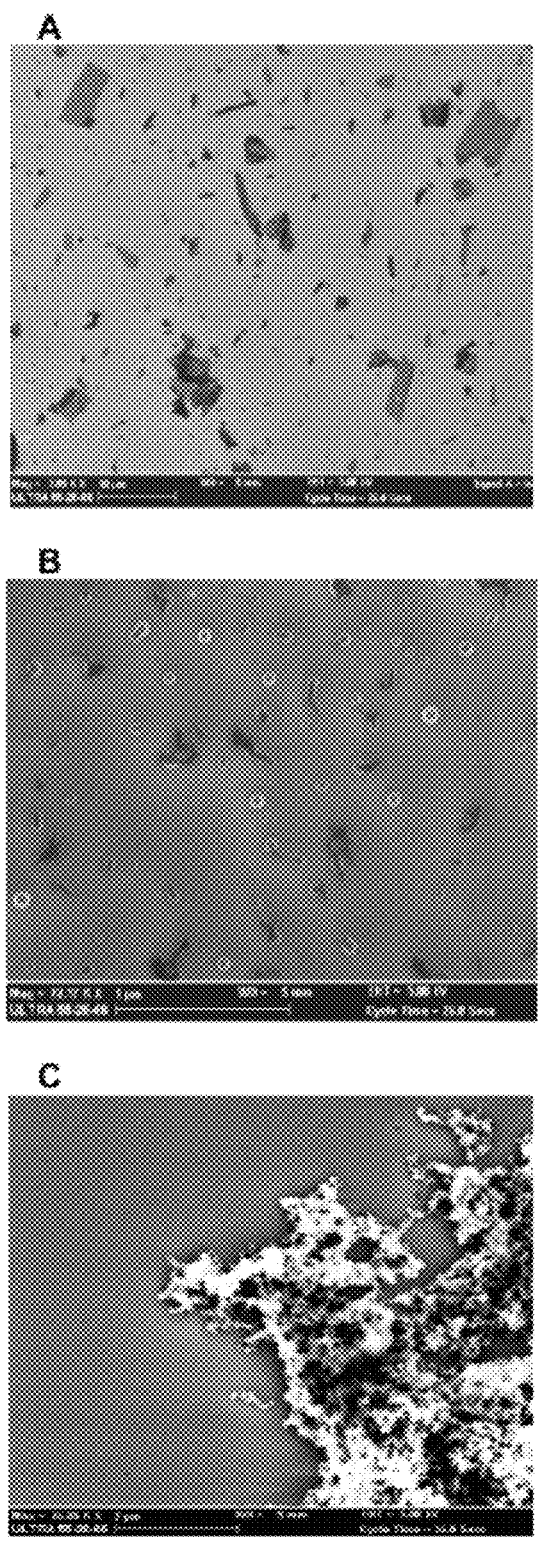
FIG. 7 shows the results of an experiment to demonstrate that a 2-fold peptoid 36-mer is capable of self-assembling into a two-dimensional sheet structure, while 3-fold and 4-fold peptoid 36-mers are each incapable of self-assembling into a two-dimensional sheet structure. Panel A shows the two-dimensional sheet structures formed by the 2-fold peptoid 36-mer. Panel B shows the structures formed by the 3-fold peptoid 36-mer. Panel C shows the structures formed by the 4-fold peptoid 36-mer.

Self-assembly into Two-dimensional Sheets 2-fold peptoid oligomers, of the present invention, are capable of self-assembly into two-dimensional sheets. The 2-fold 36-mer peptoids of FIG. 1 are synthesized and a 10 µM solution of the peptoids (40 mM phosphate buffer at pH 6) with a ration of 2:1 (positive:negative) is allowed to self-assemble under the conditions described. Panel A of FIG. 7 shows the resulting two-dimensional sheets formed.

Figure 4:
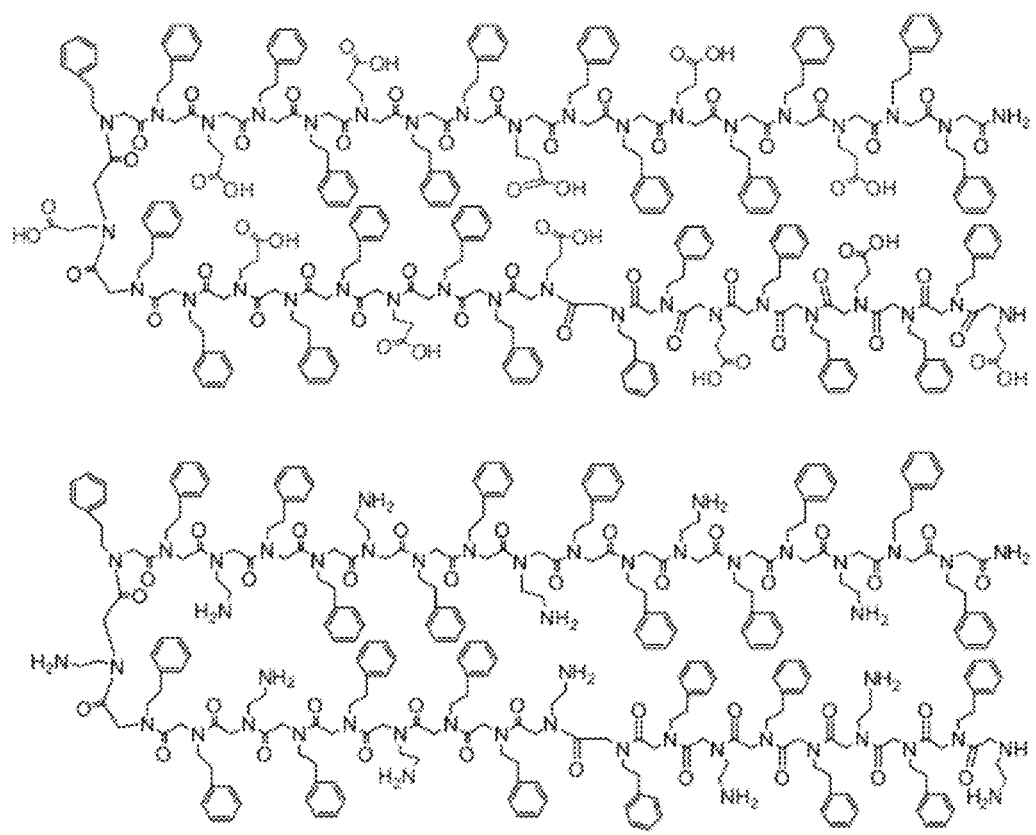
FIG. 4 shows two exemplary 3-fold peptoid 36-mers.
Figure 5:
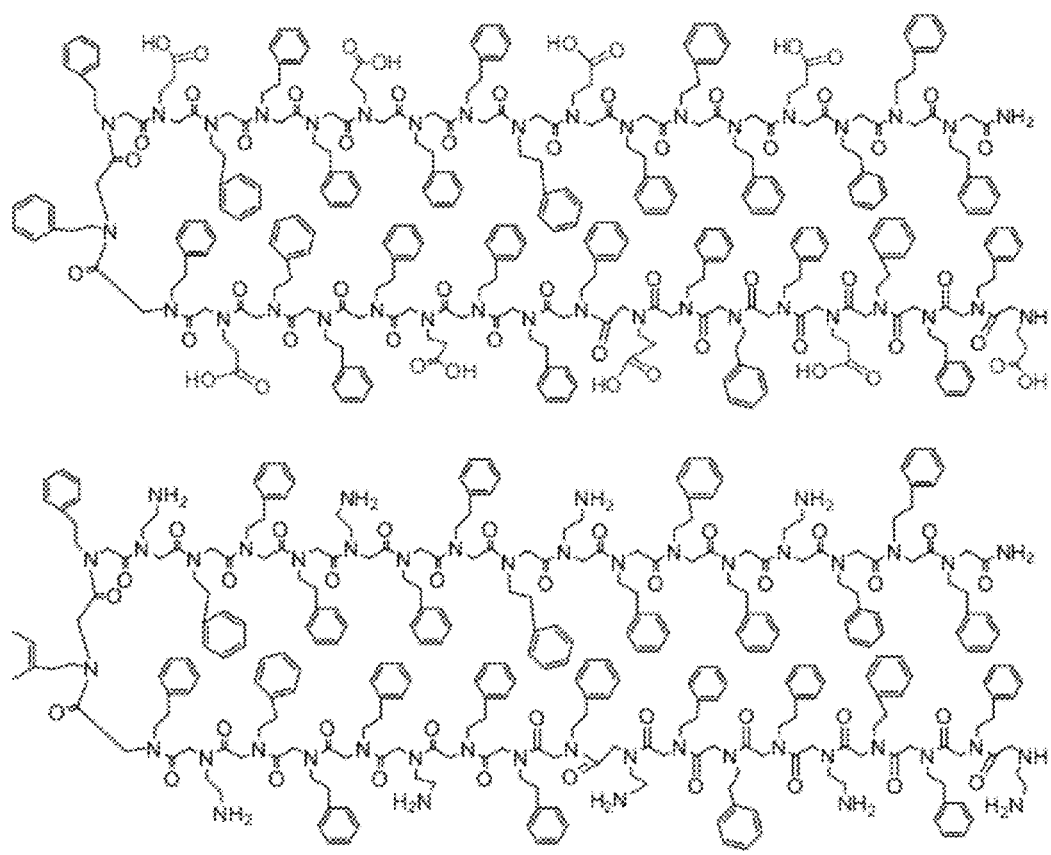
FIG. 5 shows two exemplary 4-fold peptoid 36-mers.

A 3-fold peptoid 36-mer and a 4-fold peptoid 36-mer (represented in FIGS. 4 and 5, respectively) are synthesized and each is subjected to the identical self-assembly condition of the 2-fold peptoid oligomer described above. Panel B and C of FIG. 7 show the resulting structures formed for each. Neither 36-mers form two-dimensional sheets.

This experiment demonstrates that the 2-fold peptoid oligomers of the present invention, and not 3-fold or 4-fold peptoid oligomers, are capable of self-assembling into two-dimensional sheet structures.

EXAMPLE 3

Assembly of Two-dimensional Sheets

Two-dimensional sheets are assembled using the methods described herein. For the assembly of sheets, $(Nae-Npe)_{18}$ and $(Nce-Npe)_{18}$ are each dissolved in the same aqueous buffer at the same concentration and an equal volume of the former is added rapidly to the latter at room temperature.

The sheets assembled showed physical stability against a variety of conditions as monitored by fluorescence microscopy. Sheets maintained their planar structure against 30 min. sonication at 105W and at up to 50% acetonitrile in water. The effects of stability in methanol did not present as sharp a transition as with acetonitrile. XRD analysis showed that the sheets were still crystalline in up to 50% methanol/water mixture. At 60% to 80% methanol, the sheets aggregated but did not completely dissolve. Sheets evaporated and dried on a Si wafer are observed to melt at 215° C. when exposed to the air.

Nile Red, an environmentally-sensitive dye whose fluorescence intensity increases substantially when it is localized in a hydrophobic environment, is used at a final concentration of 1 μM to stain the sheets for imaging. The solutions are dropped onto pre-cleaned microscope slides and imaged under epifluorescence illumination with an Olympus IX81 inverted microscope (Olympus USA Inc., Center Valley, Pa.) fitted with an Andor iXonEM+EMCCD camera (Andor™, South Windsor, Conn.). Once loaded onto the microscope slide, sample solutions are covered with a coverslip and allowed to sit undisturbed for twenty minutes to one hour to allow the sheets to completely settle onto the surface. For a 0.1 mM peptoid sheet preparation, the coverage of sheets on the microscope slide can be fairly high.

Fluorescence optical microscope images of sheets that are free floating in aqueous solution are obtained. The images are taken from different areas of the same sample and are representative examples of the number of sheets which can be produced using 0.1 mM concentrations of $(Nce-Npe)_{18}$ and $(Nae-Npe)_{18}$. The sample is imaged in a small chamber using Nile Red (0.5 μM) as a fluorescent stain and is not further concentrated. The images show that sheet coverage of the microscope slide surface is uniformly high, sometimes forming multiple layers, throughout the sample.

EXAMPLE 4

Conjugating Dye to Peptoid Oligomers

The present invention provides for the synthetic flexibility to functionalize precise atomic locations and to incorporate complex sequence information into two dimensional crystalline sheets. One can label each peptoid site-specifically with a dye molecule, such as Alexa Fluor® 555 and Alexa Fluor® 647. It enables one to monitor the kinetics and study the mechanism.

$(Nae-Npe)_2-Nse-Npe-(Nae-Npe)_{15}$ and $(Nce-Npe)_2-Nse-Npe-(Nce-Npe)_{15}$ are synthesized by substitution of the solvent-exposed 5th position of the sheet-forming 36-mers with N-(2-mercaptoethyl)glycine (Nse). S-trityl-2-mercaptoethylamine is used as the submonomer at position 5 and is prepared by the method of M. Maltese (*J. Org. Chem.* 66, 7615 (2001)), hereby incorporated by reference. After the synthesis, Alexa Fluor® 555 and Alexa Fluor® 647 dyes (in maleimide form, Life Technologies Corp., Carlsbad, Calif.) are conjugated to thiol functional group of HPLC-purified $(Nae-Npe)_2-Nse-Npe-(Nae-Npe)_{15}$ and $(Nce-Npe)_2-Nse-Npe-(Nce-Npe)_{15}$ peptoids, respectively (D. G. Smyth et al., *Biochem. J.* 91, 589, (1964), hereby incorporated by reference). Both reactions were purified to more than 95% homogeneity by reversed-phase HPLC as previously described. Peptoid oligomers are synthesized on an automated robotic synthesizer using the solid-phase submonomer method as described in by R. N. Zuckermann, J. M. Kerr, S. B. H. Kent, W. H. Moos (*J. Am. Chem. Soc.* 114, 10646 (1992)), hereby incorporated by reference.

Figure 8:
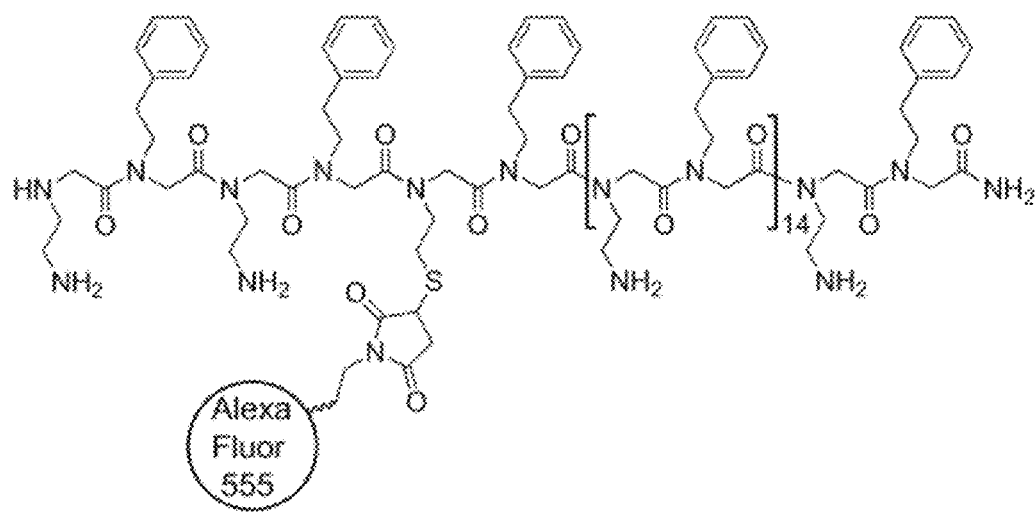
FIG. 8 shows the structure of Alexa Fluor® 555-conjugated $(Nae-Npe)_2-Nse-Npe-(Nae-Npe)_{15}$.
Figure 9:
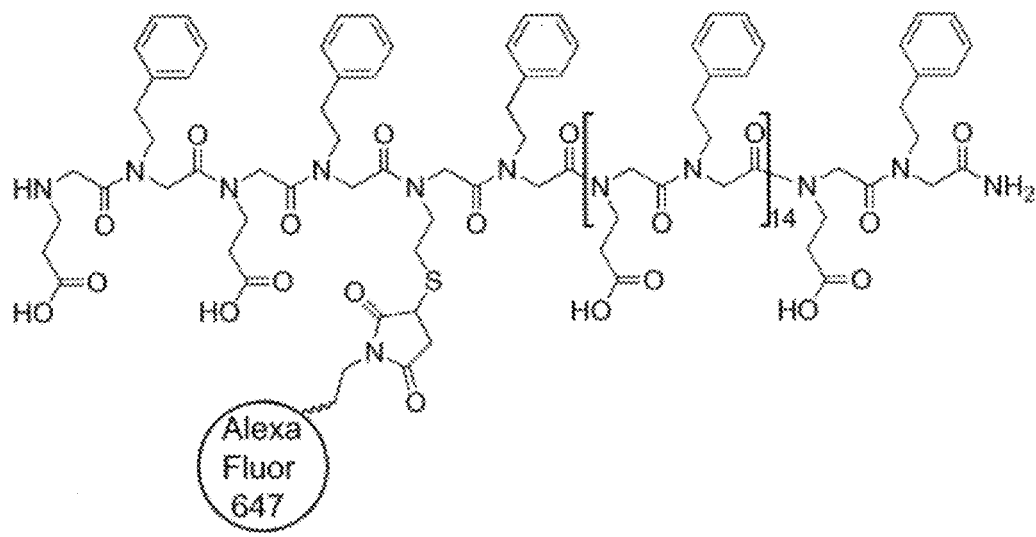
FIG. 9 shows the structure of Alexa Fluor® 647-conjugated $(Nce-Npe)_2-Nse-Npe-(Nce-Npe)_{15}$.

FIGS. 8 and 9 show the structure of Alexa Fluor® 555-conjugated $(Nae-Npe)_2-Nse-Npe-(Nae-Npe)_{15}$ and Alexa Fluor® 647-conjugated $(Nce-Npe)_2-Nse-Npe-(Nce-Npe)_{15}$, respectively.

The capability to tailor the side chains with various functionalities is not limited to the above example. The biological functional motifs including peptide sequence also can be incorporated and various side chains can be incorporated.

EXAMPLE 5

Folding of a Single-Chain, Information-Rich Polypeptoid Sequence into a Highly-Ordered Nanosheet The design and synthesis of protein-like polymers is a fundamental challenge in materials science. A means to achieve this goal is to create synthetic polymers of defined sequence where all relevant folding information is incorporated into a single polymer strand. We present here the aqueous self-assembly of peptoid polymers into thin two-dimensional highly ordered nanosheets, where all folding information is encoded into a single chain. The sequence designs enforce a two-fold amphiphilic sequence periodicity, while varying the patterning of charged residues: alternating charges and contiguous segregated charged domains (block patterning). Sheets form between pH 5 and 10 with the optimal conditions being pH 6 for the alternating sequence and pH 8 for the block. Once assembled, the nanosheets remain stable between pH 6 and 10 with observed degradation beginning to occur below pH 6. The alternating charge nanosheets remain stable up to concentrations of 20% acetonitrile, while the block pattern displayed greater robustness remaining stable up to 30% acetonitrile. These observations are consistent with expectations based on considerations of the molecules' electrostatic interactions. This example represents an important step in the construction of abiotic materials founded on biological informatic and folding principles.

Introduction

Mimicking biology's ability to form highly defined, functional three-dimensional architectures, such as proteins, remains an important goal of modern materials science. Fulfillment of this challenge could potentially provide stable, low-cost synthetic materials imbued with the ability to exhibit specific, high-affinity molecular recognition and catalytic activity that rival proteins. Mimicry of biology's architectural control would not only provide new functional materials, it would deepen our insight into protein structure and the rules that govern the kinetics and thermodynamics of their folding.

This example describes our creation of two-dimensional ordered nanosheets from a single-chain synthetic polymer, as a means to examine the degree to which the same assembly and informatic principles of biology can be applied to the folding of synthetic systems. By controlling main chain polymer length, side chain structure and functionality, in conjunction with sequence patterning, we hope to exploit the hierarchical nature of protein folding[1] to generate functional materials. Studied for almost fifty years,[2] computational methods have greatly assisted the understanding of α-polypeptide folding;[3-5] however, the theory to predict the folding and self-assembly of non-natural foldamers is still in its infancy.[6] Therefore, expanding our understanding of biomimetic polymer folding and assembly must currently be done empirically.

Figure 10:
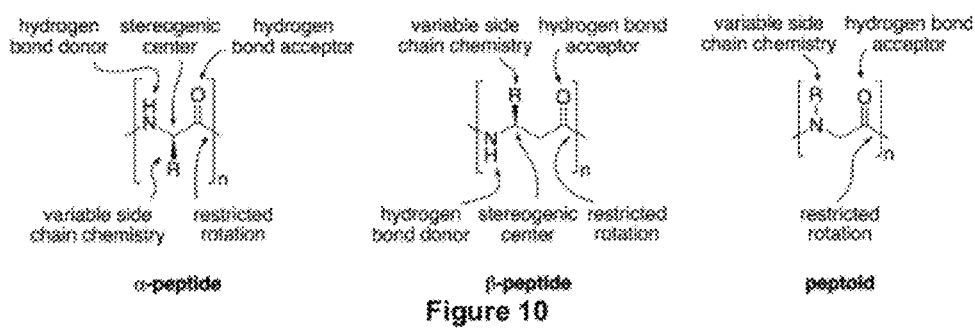
FIG. 10 shows comparison of the monomeric building blocks that comprise polypeptides, β-peptides and peptoids, and the architectural information encoded in their structure.

In the realm of non-natural foldamers, peptoids' (N-substituted polyglycines) ease of synthesis makes them prime candidates for empirical elucidation of polymer folding rules, as they can be readily assembled from commercially available materials using the solid-phase submonomer method.[7] This stands in contrast to the more sophisticated β-peptides, which require multistep protected monomer syntheses.[8] While peptoids may lack some of the inherent structural programming of α- and β-peptides (FIG. 10), their synthetic flexibility and efficiency make them an excellent choice to assist in the advancement of biomimetic architectural assembly.

Following nature's blueprint, many investigators are creating high molecular weight synthetic polymers that possess the same monomeric structure, sequence sophistication, and patterned amphiphilicity to access highly ordered biomimetic structures. Most of the activity in this recent area is based on β-peptide or peptoid chemistry. The β-peptide monomer possesses the same structural sophistication and attributes of α-peptides albeit with the inclusion of one additional methylene unit. These parallel attributes culminate in well-defined helical secondary structures,[9,10] including reports of constrained tertiary interactions using disulfide bonds,[11] metal chelation,[12] and Watson-Crick base pairing.[13] Schepartz and coworkers designed amphiphilic β-peptide sequences that assemble into helical bundles[14] and a crystalographically defined coiled-coil quaternary structure.[15] Furthermore, they linked adjacent helices together in an anti-parallel fashion[16] improving the self-association of the now tetrameric helical bundles 10-fold, thus highlighting the advantages of single chain encoded polymers in the assembly of higher order structures.

Peptoids assume secondary and higher order structures despite their greater conformational freedom, inherent lack of chirality, and absence of backbone hydrogen bond donors as compared to α- and β-peptides. In order to affect main chain curvature, and thus access helical structure, bulky branched chiral substituents are used as side chains[17-22]. By employing a three-fold amphiphilic sequence periodicity, our lab previously constructed peptoid helices that fold cooperatively into helical bundles[23], which were further stabilized by conjugative chemistry to create a single-chain structure.[24] In an extension of this work, a similar helical bundle motif was used to create a high-affinity zinc-binding site serving as a step toward generating biomimetic nanostructures with enzyme-like functions.[25]

Figure 11:
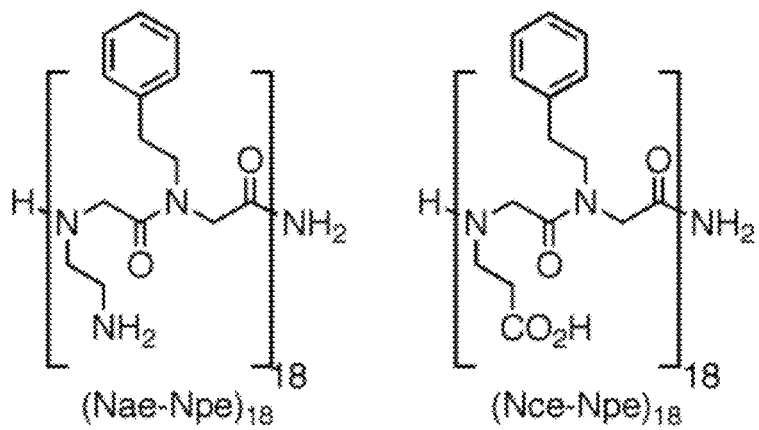
FIG. 11 shows oppositely charged pair of polypeptoids that were previously reported[27] to self-assemble into highly ordered nanosheets.

Until recently, β-sheet mimetic architectures have remained elusive as they necessitate the assembly of more challenging chain-chain interactions whereas α-helices only require intra-chain organization. Our lab recently used peptoids to exploit the two-fold periodicity common in β-sheets[26], to create water-soluble two-dimensional nanosheets only two molecules thick.[27] This highly ordered material was created via the aqueous complexation of two oppositely-charged peptoid strands, which were comprised of only three monomers, N-(2-aminoethyl)glycine (Nae), N-(2-phenethyl)glycine (Npe), and N-(2-carboxyethyl)glycine (Nce). The strands, (Nae–Npe)$_{18}$ and (Nce–Npe)$_{18}$, depicted in FIG. 11, assemble into a bilayer, in which the primary driving force for assembly is the burial of the hydrophobic residues and exposure of the ionic, hydrophilic side chains to water. This two-fold periodicity coaxes the polymer into a fully-extended chain conformation to generate a molecular scale linear amphiphile. Since the nanosheet's structure remains intact in the absence of water, it stands to reason that the exposed charged hydrophilic side chains also contribute, via electrostatics, to the overall stability of the supramolecular structure.

The use of two separate strands raises the question of whether this folding information can be encoded into a single polymer chain, as is often the case with protein biopolymers. The use of binary ionic polymer complexation is well studied and has resulted in many new supramolecular materials, such as polyelectrolyte multilayers.[28,29] The advantage of single chains, however, is that it enables more defined biophysical measurements and mechanistic experiments to be performed. Furthermore, it takes us one step closer to the biological principal of programming all the folding instructions into a single polymer chain. Ultimately, we aim to design and synthesize sequences that can not only fold, but also exhibit highly specific molecular recognition and catalysis. In our efforts to achieve these goals, we present here an important step in generating information-rich single chain polymers that fold into higher order structure via the encoded folding principles of biology.

Results and Discussion

Figure 12:
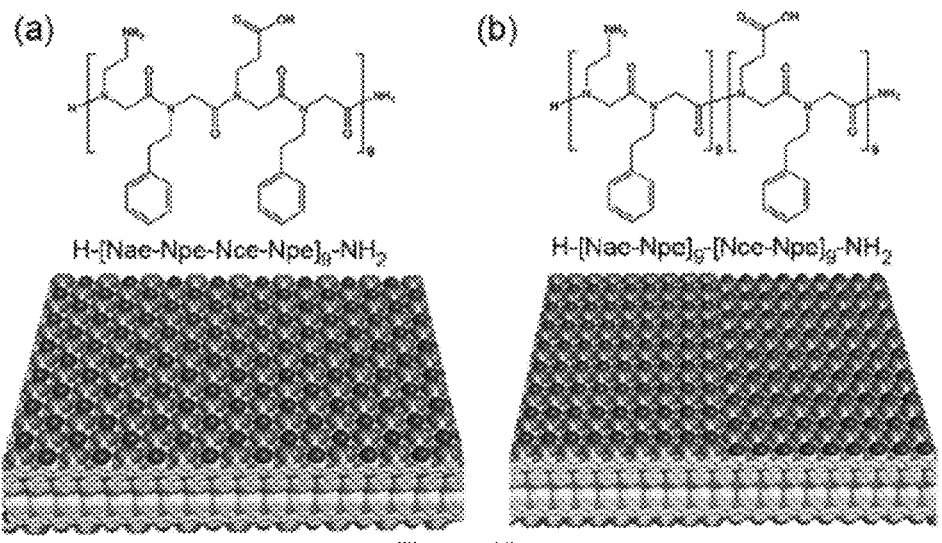
FIG. 12 shows single-chain peptoids that form nanosheets: (a) alternating charge and (b) block charge sequences. A model of a section of each type of sheet is shown, illustrating the differences in the proposed alignment of the chains. While both designs can accommodate oppositely charged groups to be in close proximity, the alternating charge sheets would be expected to have less long-range order (yellow=carbon, red=oxygen, blue=nitrogen).

Design Strategy and Synthesis. With our objective to obtain high molecular weight, single strand, information encoded polymers, we sought to retain and combine the critical design elements from our initial system: hydrophobics, electrostatics, and a two-fold amphiphilic sequence periodicity[27]. We synthesized two constructs versions containing the same composition and periodicity, but with different charge distributions via the submonomer method: a block charge structure, (Nae–Npe)$_9$–(Nce–Npe)$_9$, and an alternating charge structure, (Nae–Npe–Nce–Npe)$_9$ (FIG. 12). Both of these single-chain polypeptoid constructs are significantly more sophisticated with respect to their monomer sequence information content than typical block and alternating copolymers. The synthesis of these complex sequence patterns with no polydispersity, is a level of precision that remains out of reach of traditional polymer chemistry.

The block charge structure, (Nae–Npe)$_9$–(Nce–Npe)$_9$, possesses two oppositely-charged stretches of like-charged hydrophilic side chains, providing large recognition domains for strands to interact and pattern themselves laterally according to charge complementarity. These contiguous charged segments may also enforce polymer linearity through intrastrand electrostatic repulsion. In these two ways this system is similar to our original binary nanosheet system[27]. The alternating charge structure, (Nae–Npe–Nce–Npe)$_9$ retains the ability to mutually associate in a manner that locally satisfies charge-charge interactions, but lacks the large stretches of like-charged domains carried by the block molecule. We expect this difference to be significant (see next section). Interestingly, peptidic versions of the alternating charge sequences (e.g. EFKF oligomers) do not form sheets at all and instead form fibrils or hydrogels.[30,31] These two extreme patterns containing the same composition and amphiphilic periodicity should provide insight into the importance of the molecules' local electrostatic charge environment.

Figure 13:
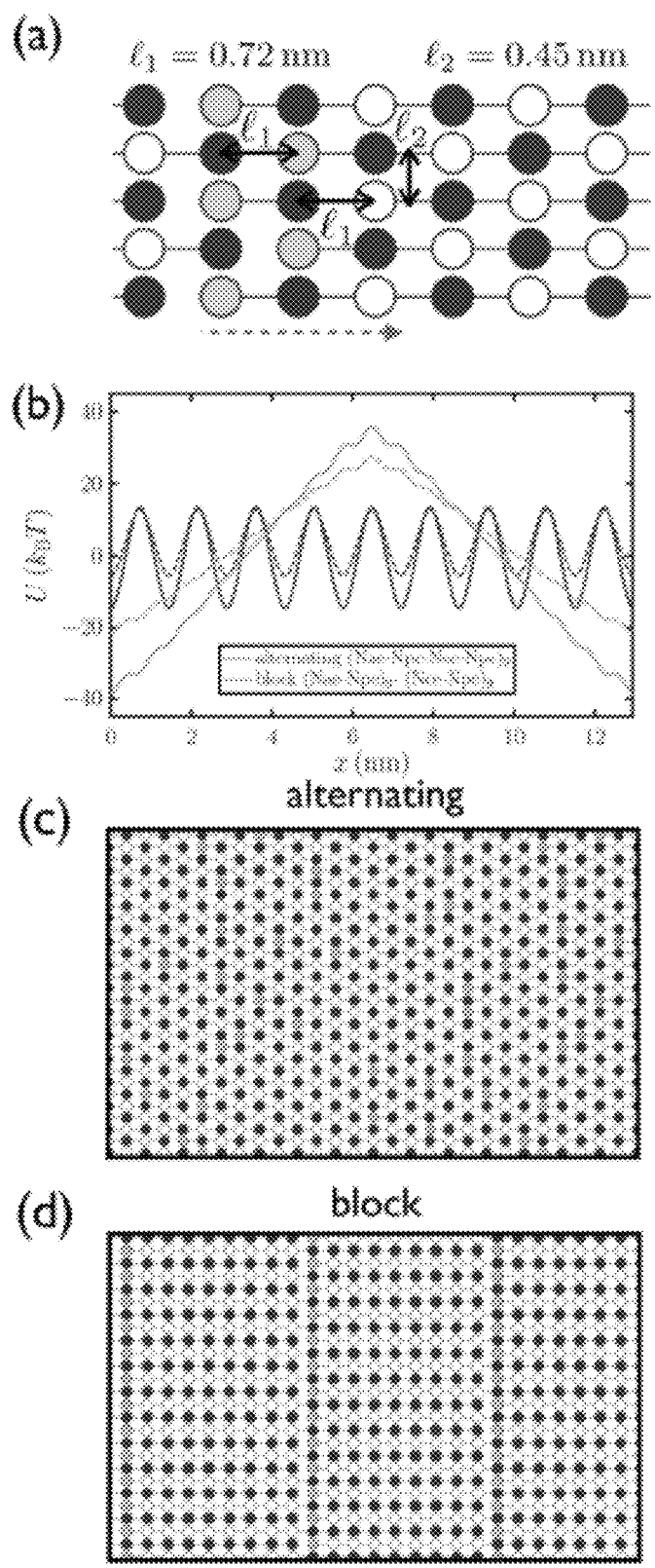
FIG. 13 shows calculations of the electrostatics of model nanosheets show the block charge nanosheet to be more stable than the alternating charge nanosheet. (a) Geometry of model sheet (b) Electrostatic energy U of a peptoid in a row of a sheet as that row is slid a distance x with respect to the others. (c and d) Monte Carlo simulations that allow peptoids to sample different positions reveal the equilibrium configurations of (c) the alternating charge sheet to be less ordered than (d) the block charge sheet.

Expected Consequences of Charge Patterning. We expect sheets formed from alternating and block hybrid molecules to have different electrostatic properties, because of their differing charge patterns. We can explain this expectation using a simple simulation model based on the consideration of the two spatially extended dimensions of a sheet, and only one of the sheet's faces (FIG. 13). We set up an extended ordered monolayer of chains of 18 bound charges, modeling peptoids that are 36 residues long. Spacings between charges and chains were taken from experimental measurements as shown (FIG. 13a). Charges interact via a screened Coulomb potential[32]. This purpose of this model is to calculate the electrostatic energy associated with specified patterns of peptoids (assuming that such a sheet has already self-assembled). We neglect bending of chains and other spatial fluctuations that might lead to the breakdown of order on large length scales.

We started with a monolayer in which peptoid ends were aligned row-to-row (so that green chain ends were aligned in columns), and calculated the inter-molecular electrostatic energy of a peptoid in a given row of the monolayer as we slid that row with respect to the other rows. The direction of translation is shown by the gray arrow in FIG. 13a. In our calculations the monolayer was periodically replicated in both dimensions, in imitation of bulk surroundings, and so such a translation affects the pattern of charges displayed by the monolayer but does not disturb the integrity of the monolayer (i.e. there are no 'edges' of the sheet in this calculation). The electrostatic energy U of a peptoid in the translated row was calculated for the alternating hybrid (blue lines) and the block hybrid (green lines), as a function of the distance of row translation x (FIG. 13b). Distance x=0 describes the initial ordered monolayer, and the maximum value of x shown corresponds to the sliding of a row of the monolayer by one peptoid length. We show results at 150 mM NaCl concentration for all residues ionized (solid lines) and for an ionization probability of the COOH residue of 61% (dashed lines). These two choices correspond roughly to pH 7 and 5, respectively (see Materials and Methods).

Two features are apparent from FIG. 13b. The first is that the favorable electrostatic energy of a block molecule sheet (approx. 38 $k_B T$ per peptoid when residues are fully ionized) exceeds that of the alternating molecule sheet (approx. 15 $k_B T$ per peptoid). This is chiefly because charges in the interior of each block molecule possess (in rows above and below) only opposite charges as their nearest- and next-nearest neighbors (FIG. 13d). By contrast, charges in the alternating peptoid monolayer possess like charges as their next-nearest neighbors in rows above and below (FIG. 13c). We expect that a molecule's intra-molecular interaction plays a less prominent role in determining sheet patterning, because its charges are linked together chemically. At a reduced state of COOH group ionization (dotted lines in FIG. 13b), the electrostatic energy of each type of sheet is still favorable, but that of the alternating molecule is only about 5 $k_B T$ per molecule.

The second feature apparent from FIG. 13b is that the different charge periodicities of the two types of molecule are reflected in the cost required to translate a row of peptoids within a sheet. For the alternating molecule, sliding rows by twice the backbone charge-charge distance meets with no energetic cost. For the block molecule, any translation less than one molecule length is energetically unfavorable. We therefore expect that the patterns formed within equilibrated sheets of alternating and block molecules will be different. This expectation is illustrated in FIGS. 13c and 13d, which show sheet fragments from equilibrated Monte Carlo simulations (for full residue ionization) of alternating and block molecules, respectively (see Materials and Methods). The alternating molecule adopts a pattern in which chain ends (green) show no correlation from row to row (FIG. 13c), while the rows of the block molecule sheet are strongly correlated (FIG. 13d). This high degree of local order suggests that the block molecule is a good candidate for creating sheets that display spatially precise, chemically selective regions.

The model considered here is clearly idealized, and neglects potentially important features of molecule flexibility and hydrophobicity. However, we believe it to be a good starting point for interpretation of our experimental results.

Figure 14:
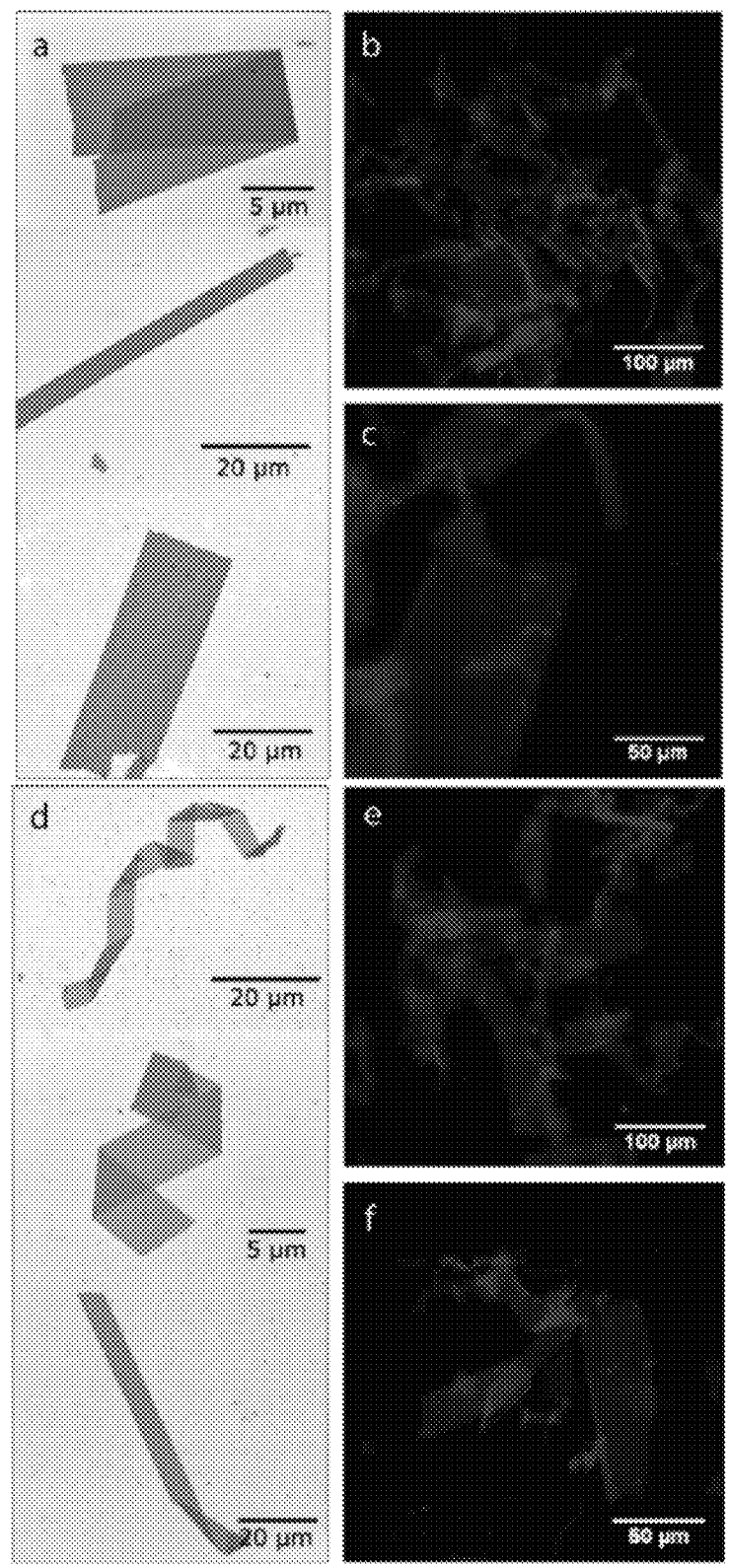
FIG. 14 shows imaging of peptoid nanosheet morphology by scanning electron microscopy (a, d) and fluorescence optical microscopy (b-c, e-f). Sheets were formed from a 20 mM peptoid solution in 10 mM Tris, 100 mM NaCl, pH 8.0. (a-c) Alternating charge sheets made from (Nae-Npe-Nce-Npe)$_9$, (d-f) block charge sheets made from (Nae-Npe)$_9$-(Nce-Npe)$_9$.

Structure of Sheets. Sheets were assembled in dilute aqueous solution and analyzed by a variety of techniques: fluorescent optical microscopy, scanning electron microscopy (SEM) and powder pattern X-ray diffraction (XRD). In comparison to the previously reported two-component system, the single-chain peptoid nanosheets form at an approximately three-fold slower rate. Fluorescent optical microscopy of both the alternating charge and block charge nanosheets, using Nile Red, an extrinsic environmentally sensitive dye, showed the presence of sheets with characteristic straight edges (FIG. 13). Both the block and alternating sheets exhibit typical edge lengths between 10 and 100 microns. Currently, we are unable to control this size distribution; however, investigations are currently under way and will be reported in due course. SEM showed that the sheets retained the same parallel edges as the original two-component system, indicating that we have formed a similar supramolecular morphology from different molecular materials (FIG. 14).

Figure 15:
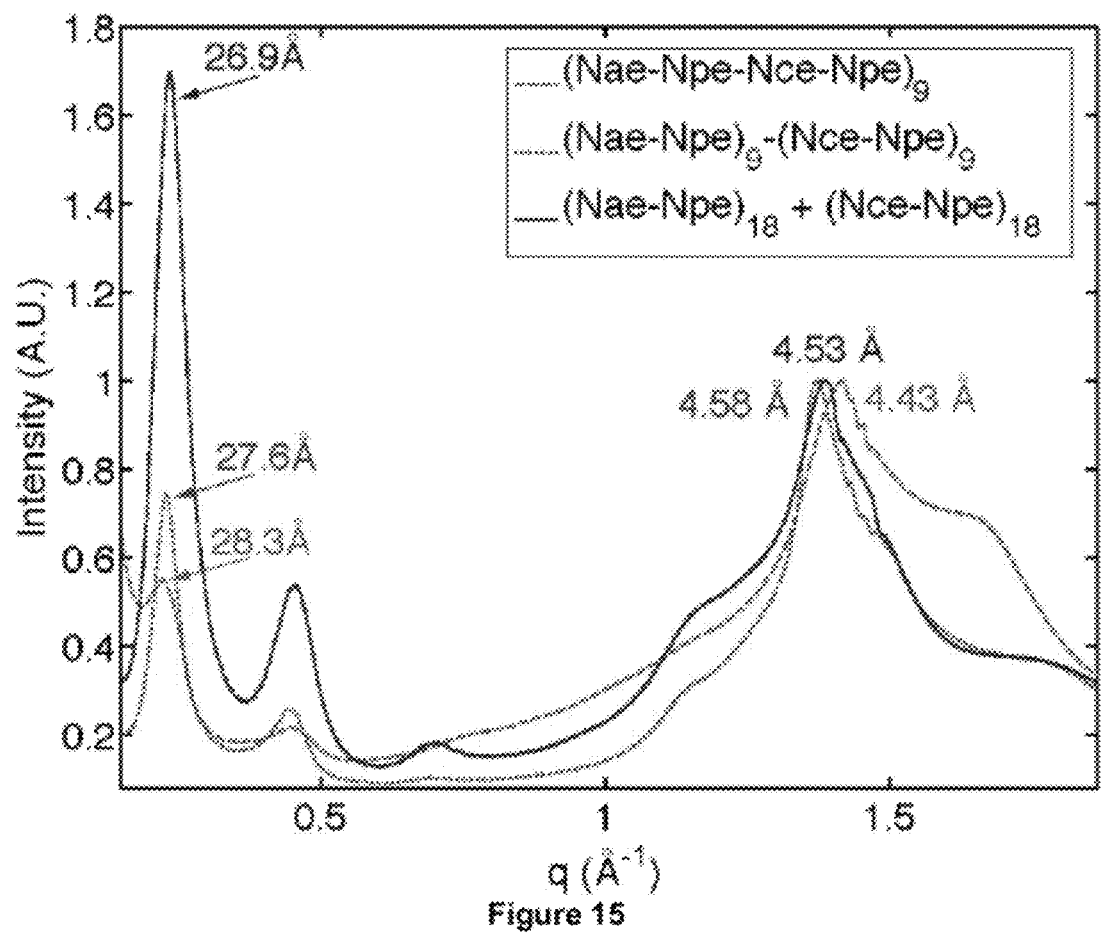
FIG. 15 shows powder X-ray diffraction analysis of concentrated pellets of the alternating sheets (Nae-Npe-Nce-Npe)$_9$, block sheets (Nae-Npe)$_9$-(Nce-Npe)$_9$, and two-component sheets (Nae-Npe)$_{18}$+(Nce+Npe)$_{18}$, normalized to the amplitude of the 4.4-4.6 Å peak.
Figure 16:
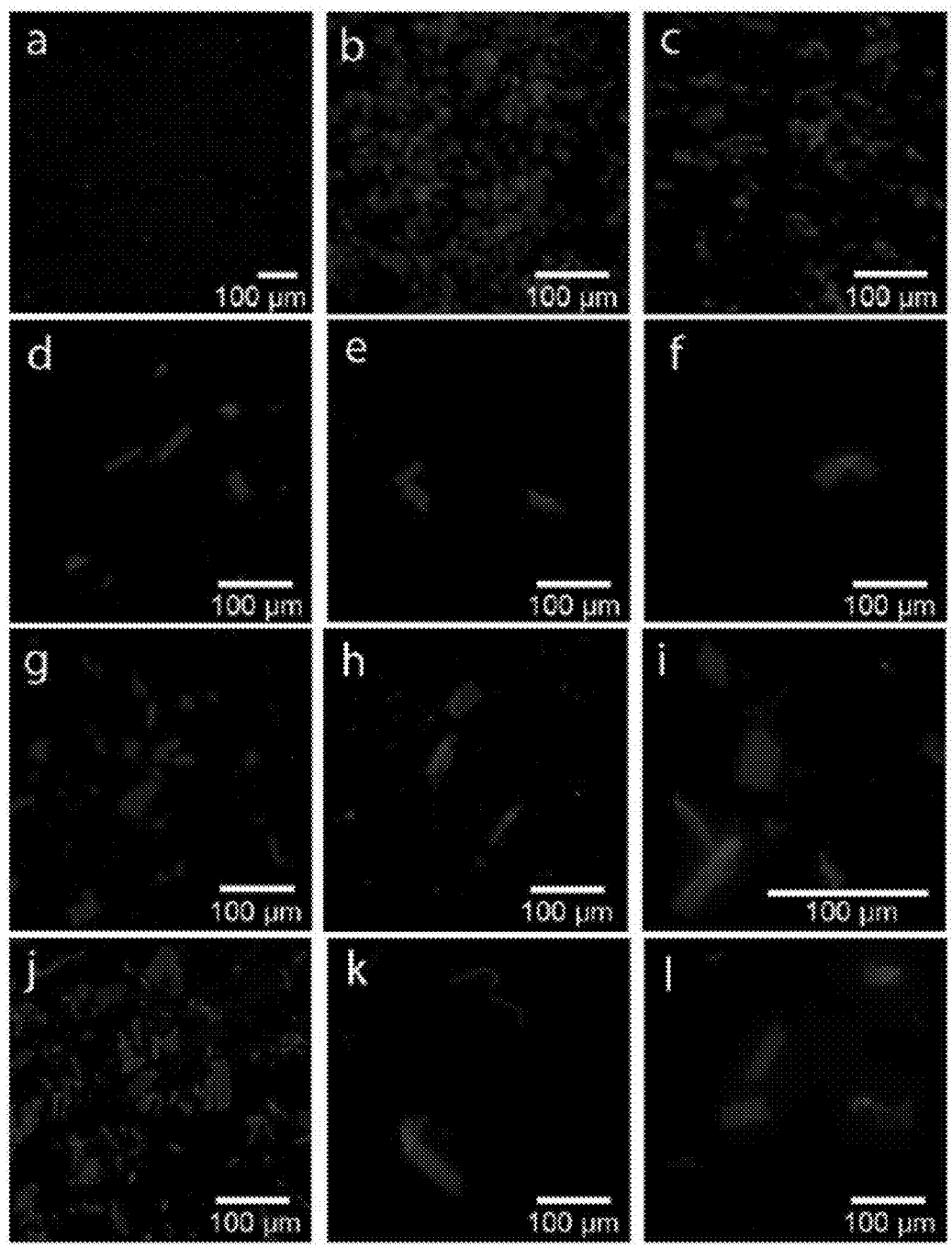
FIG. 16 shows sheet assembly as a function of pH monitored by fluorescence optical microscopy. (a-f) Images of the alternating charge sheets (Nae-Npe-Nce-Npe)$_9$ assembled at (a) pH 5, (b) pH 6, (c) pH 7, (d) pH 8, (e) pH 9, and (f) pH 10. (g-l) Images of the block charge sheets (Nae-Npe)$_9$-(Nce-Npe)$_9$ assembled at (g) pH 5, (h) pH 6, (i) pH 7, (j) pH 8, (k) pH 9, and (l) pH 10.
Figure 17:
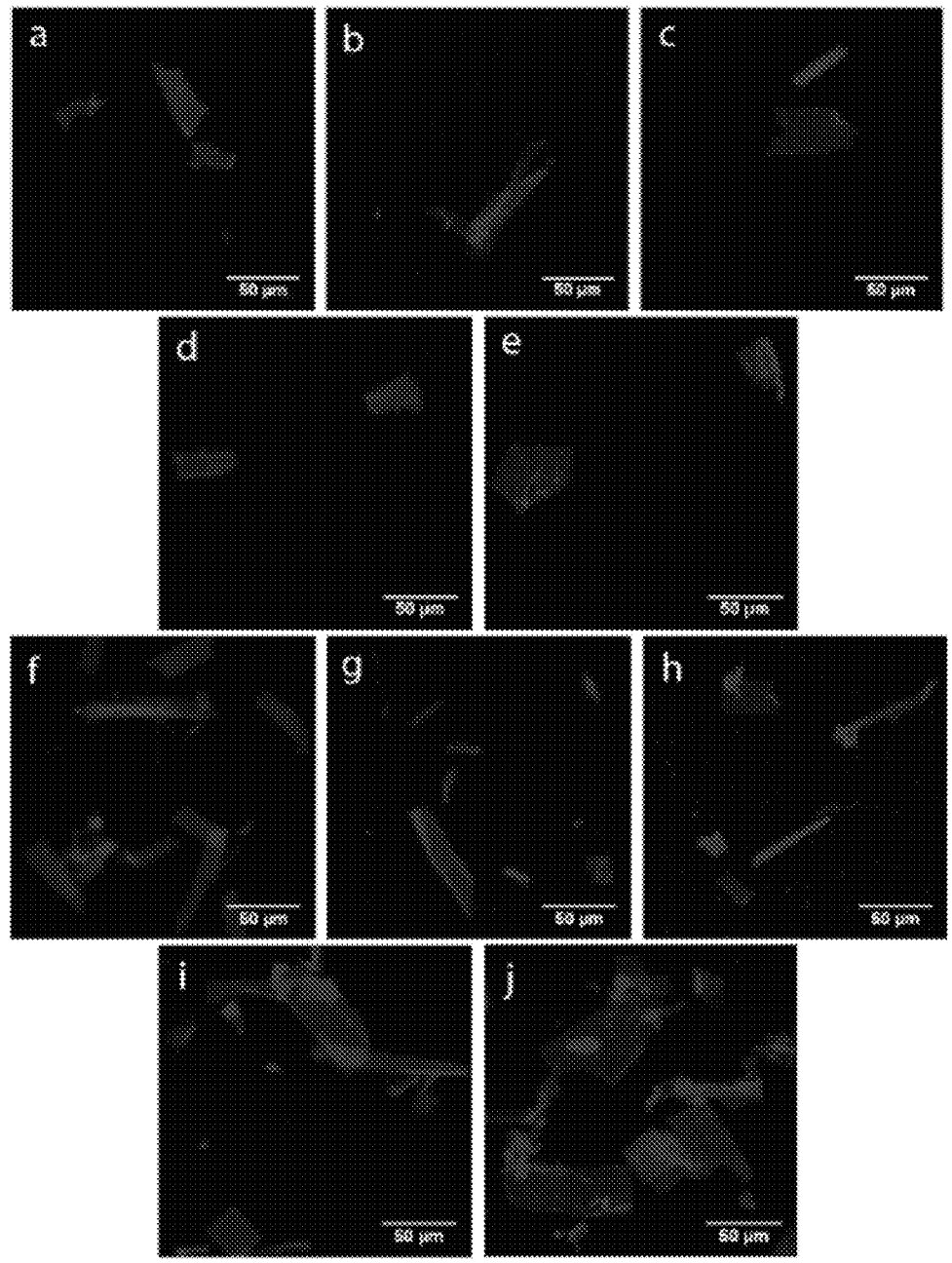
FIG. 17 shows sheet sensitivity to pH as monitored by fluorescence optical microscopy. Images of the alternating charge sheets (Nae-Npe-Nce-Npe)$_9$ at (a) pH 5, (b) pH 7, (c) pH 8, (d) pH 9, and (e) pH 10. Images of the block charge sheets (Nae-Npe)$_9$-(Nce-Npe)$_9$ at (f) pH 5, (g) pH 6, (h) pH 7, (i) pH 9, and (j) pH 10.

The molecular structure of the nanosheets was analyzed by powder pattern X-ray diffraction at the Advanced Light Source. The XRD of both the alternating and block charge nanosheets indicate that the materials possess a high degree of order and a structure similar to that of the two-component nanosheets (FIG. 15). Both hybrids possess a 2.7-2.8 nm peak that corresponds to the thickness of the bilayer, and a 4.4-4.6 Å peak that corresponds to the inter-strand distance between polymer chains. The XRD spectra are remarkably similar to that of the previously-reported binary nanosheet system[27] indicating a comparable molecular structure. Examination of the XRD spectra of the materials in the region of the 4.5 Å peak suggests that sheets built from block charge chain and the original two-component nanosheets are more ordered locally than are sheets built from the alternating charge chain. This difference in order may result from a different in the electrostatic driving force for regular association of polymers expected of the block and alternating sheets (FIG. 13).

pH Dependence on Assembly. The charge state of the molecule should affect the assembly of the nanosheets as electrostatic forces are likely to play a prominent role in sheet stability. If correct charge complementarity were frustrated, this would likely result in lower sheet stability, or may even prevent sheets from forming at all. To explore this notion we examined sheet formation over a pH range of 5-10. We noticed a striking difference in the pH optima and quantity of sheets formed between the alternating and the block charge chains (FIG. 16). The alternating charge chain exhibited maximum sheet production at pH 6 and 7, while pH 5, 9, 10 showed few or no sheets present indicating that the charged state of the polypeptide has a significant effect on the assembly rates of sheets. In contrast, the block charge chain showed less dependence on pH. It formed sheets over the full range of pH considered, and formed them most abundantly at pH 8. This difference in sensitivity to charge state is consistent with our expectations based on considerations of electrostatic energy (FIG. 13). We expect the electrostatic driving force for association of the block charge chains into sheets to be greater than that of the alternating charge chain, and we expect that changes in peptoid charge states impair assembly of the alternating chain before they impair assembly of the block chain.

pH Stability of Sheets. Electrostatic and hydrophobic interactions clearly play significant roles in the stability of sheets. By modulating the pH we affect the charge density of the sheets providing insight into the effects of electrostatic forces. Sheets formed under optimal conditions, pH 6 for the alternating charge chain and pH 8 for the block charge chain, were dialyzed using a 100 kD membrane with the appropriate buffer to a pH between 5-10 until the desired pH was obtained. The sheets were then maintained at the defined pH for 17 h, whereupon they were examined using fluorescence optical microscopy (FIG. 17). The block charge chain displayed remarkable resilience to pH, having sheets present at all measured pH values with the only evidence of decomposition occurring at pH 5. This weak pH dependence is likely a result of the large contiguous charged domains. We expect spatially extended regions of such domains to remain energetically favorable even when charge states are reduced considerably (FIG. 13). In contrast, the alternating charge sheets showed no appreciable degradation at pH 7 and 8, but at pH 5, 9, and 10 sheets were present in decreased quantity and size. These data suggest that that the electrostatic environment felt by a charge in an alternating charge sheet is generally less favorable than that of the block sheet, in accord with our calculations (FIG. 13).

Figure 18:
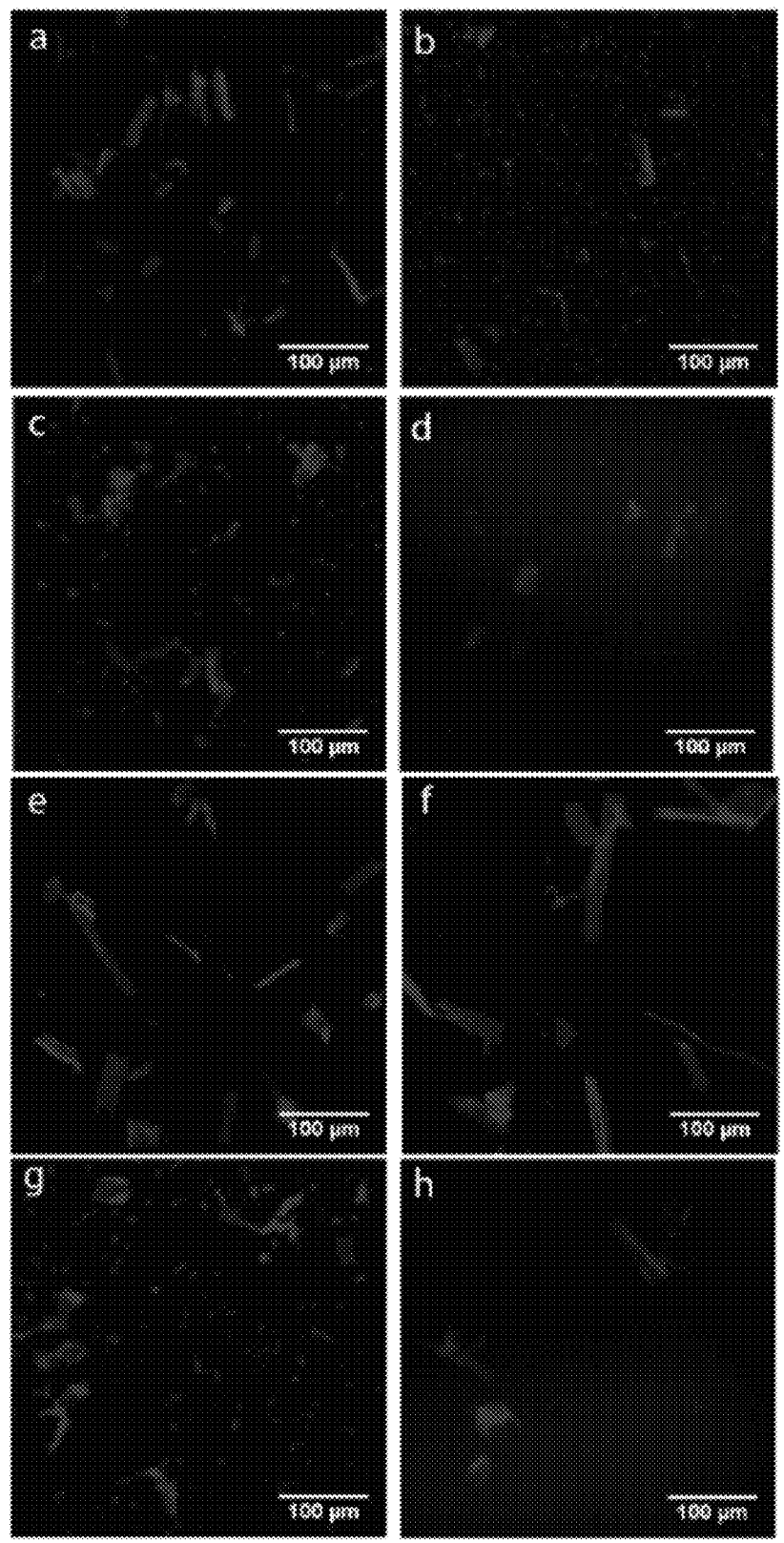
FIG. 18 shows sheet stability to acetonitrile as monitored by fluorescence optical microscopy. Images of the alternating charge sheets (Nae-Npe-Nce-Npe)$_9$ at (a) 10%, (b) 20%, (c) 30%, and (d) 40% acetonitrile. Images of the block charge sheets (Nae-Npe)$_9$-(Nce-Npe)$_9$ at (e) 10%, (f) 20%, (g) 30%, and (h) 40% acetonitrile.

Sheet stability toward acetonitrile. Hydrophobic solvents, such as acetonitrile, serve as a tool for examining the importance of hydrophobic interactions[24]. Therefore, we set out to explore the robustness of the single-chain nanosheets to increasing concentrations of acetonitrile (FIG. 18). Sheets were assembled under optimal conditions and then titrated with the appropriate amount of acetonitrile. Both the alternating and block charge sheets show no apparent degradation at 10% acetonitrile upon examination with fluorescence optical microscopy. Using erosion of straight edges as a measure for perturbation of order, in conjunction with the appearance of sheet fragments, the alternating charge sheets shows greater susceptibility to disruption at concentrations of 20% acetonitrile, with the block beginning to show loss of integrity at 30% acetonitrile. There are no discernable structures in either case at concentrations of upwards of 50% acetonitrile. The presence of acetonitrile perturbs the strength of the hydrophobic interactions present within the sheets, thus heightening the importance of electrostatic interactions in sheet integrity and stability. We attribute the difference in stability between the two hybrid sheets at 20% acetonitrile to the more favorable electrostatic environment of a block charge nanosheet (FIG. 13).

Conclusion

We have successfully demonstrated that single chain, information-rich, high molecular weight non-natural polymers create higher order sheet structures. By exploiting side chain-side chain interactions, we developed a single molecule system where polymer main chains are fully extended permitting facile interaction with neighboring strands. The two structural motifs, alternating and block charge chains, display differing sensitivities to pH and chemical denaturants with the block charge design possessing the greatest resilience and versatility. This observation is consistent with our expectation based on consideration of inter-peptoid charge-charge interactions. These highly programmed sheets advance the goal of generating abiotic materials founded on biological informatic and folding principles.

Materials and Methods

Peptoid Synthesis. Peptoid oligomers were synthesized on an automated robotic synthesizer using the solid-phase submonomer method[7,33]. In this method, the Fmoc group on Rink amide resin (0.61 mmol/g, Novabiochem, San Diego, Calif.) was deprotected with 20% 4-methylpiperidine in DMF (v/v) before starting the submonomer cycle. Peptoid synthesis on resin was carried out as follows: a 0.6 M solution of bromoacetic acid in DMF (1.13 mL in DMF, 1.35 mmol) and 0.93 eq. of N,N'-diisopropylcarbodiimide (0.20 mL, 1.25 mmol) was added to a resin-bound amine (50 µmol) and mixed for 20 min at 35° C. during acylation step of the submonomer cycle. The resin-bound bromide was then displaced with the amine submonomer by adding a 2 M solution of the amine in N-methylpyrrolidinone. The displacement reaction was carried out for 60 or 120 minutes at 35° C. for residues 1-18 or 19-36, respectively. The crude peptoid products were cleaved from the resin with 95:5 trifluoroacetic acid (TFA)/water (v/v) for two hours at room temperature. The cleavage solution was filtered and evaporated under a stream of nitrogen gas to remove the TFA. The crude peptoid product was then dissolved in a 1:1 mixture (v/v) of water and acetonitrile and subjected to further purification through reverse-phase HPLC on a Vydac C18 column (10 µM, 22 mm×250 mm), using a gradient of 30-60% acetonitrile in water with 0.1% TFA over 60 min. All final products were analyzed by analytical reverse-phase HPLC (30-55% gradient at 1 mL/min over 30 minutes at 60° C. with a C18, 5 µM, 50×2 mm column) and matrix-assisted laser desorption/ionization mass spectrometry (Applied Biosytem/MDS SCIEX 4800 MALDI TOF/TOF Analyzer) (see Table 1). The final peptoid products were lyophilized, dissolved in 100 mM HCl (aq) and then lyophilized again. This step was repeated two more times to ensure formation of the hydrochloride salt. The powder was then dissolved in a 2:1 mixture of DMSO:water in order to obtain a 2 mM stock solution stored at 4° C.

TABLE 1

Characterization of peptoid sequences by HPLC and mass spectrometry.

| Peptoid Sequence | Calculated Mass | Observed Mass | Purity[a] |
|---|---|---|---|
| (Nae-Npe-Nce-Npe)<sub>9</sub> | 4981.74 | 4981.82 | 91% |
| (Nae-Npe)<sub>9</sub>-(Nce-Npe)<sub>9</sub> | 4981.74 | 4981.24 | 95% |

[a]after HPLC purification

Sheet Formation. In a 4 mL cylindrical vial, 500 µL of 20 µM peptoid solution in 10 mM buffer and 100 mM NaCl, was prepared from the stock solution. The vials were then slowly rotated about the vertical access on an Appropriate Technical Resources RKVSD Rotamix tube rotator for three days at room temperature. Buffers used depended on pH: citiric acid (pH 5), MES (pH6), HEPES (pH7), Tris (pH 8), AMPD (pH 9) and CAPS (pH 10).

Fluorescence Optical Microscopy. Nile Red, an environmentally-sensitive dye whose fluorescence intensity increases substantially when it is localized in hydrophobic environments, was used at a final concentration of 1 µM to stain the sheets for imaging. The solutions were deposited onto pre-cleaned microscope slides and imaged under epifluorescence illumination with an Olympus 1×81 inverted microscope fitted with an Andor iXonEM+EMCCD camera. Loading 8 µL onto the microscope slide, sample solutions were covered with a coverslip and allowed to sit undisturbed for twenty minutes to one hour to allow the sheets to settle.

pH Stability Experiments. Sheets were assembled via the described method and were added to a pre-wetted Spectrum Labs Spectra/Por Float-A-Lyzer G2 dialysis apparatus with cellulose ester membranes and a molecular weight cutoff of 100 kD. The sheets were dialyzed for 3 hr in the appropriate buffer, at which time the pH of the solutions were equal. The sheet solution was then removed from the dialysis apparatus, transferred to a 2 mL cylindrical vial, maintained for 14 hr, and then subjected to fluorescence optical microscopy.

Acetonitrile Stability Experiments. Sheets were assembled via the described method and then titrated with acetonitrile to the appropriate percentage. The sheet solution was incubated for 6.5 hrs at room temperature and then subjected to fluorescence optical microscopy.

Powder XRD Analysis. X-ray diffraction data were collected at a multiple-wavelength anomalous diffraction and monochromatic macromolecular crystallography beamline, 8.3.1, at the Advanced Light Source located at Lawrence Berkeley National Laboratory. Beamline 8.3.1 has a 5 tesla single pole superbend source with an energy range of 5-17 keV. Data were collected with a 3×3 CCD array (ADSC Q315r) detector at a wavelength of 1.1159 Å. Data sets were collected with the detector 200-mm from the sample. Peptoid sheet solutions were concentrated 100 fold an Amicon Ultra centrifugal filter (100 kD MWCO, Millipore) then centrifuged at 13,200 rpm for 10 minutes. After removing the supernatant, the resulting peptoid sheet pellet was pipetted onto a Mitegen Mesh. Data was processed with custom Matlab (Mathworks) scripts.

Scanning Electron Microscopy. For scanning electron microscopy imaging, peptoid sheet solutions were dropped on plasma-treated Si substrates. The sheets were dialyzed with water beforehand to remove buffer and salt. A Zeiss Gemini Ultra-55 Analytical Scanning Electron Microscope was used with an in-lens detector and beam energies between 1 kV and 3 kV.

Simulations. Simulations were done by assembling a two-dimensional monolayer of 6×90 peptoids, periodically replicated in each dimension. Distances between charges and chains were as shown in FIG. 13a. Charges interacted via a screened Coulomb potential appropriate for three-dimensional space, $U(x)=(q_1 q_2 l_B/r) \exp(-x/l_D)$, in units of $k_B T$ at 298K. Here x is the inter-charge distance; the $q_i$ are charges in units of the elementary charge e; $l_B$ is the Bjerrum length (0.7 nm at 298 K); and $l_D$ is the Debye length (0.79 nm at the 150 mM NaCl considered)[32]. We trunctated this interaction at 5.5 Debye lengths, and verified that our results were unchanged upon increasing the cutoff distance to 6.5 Debye lengths (indicating that we incur no spurious effects from a too-short cutoff). We performed calculations for 1) the case in which all residues were fully ionized, and for 2) the case in which the $NH_3$ groups were fully ionized but the COOH groups possessed a charge of only −0.61 e. Using the Henderson-Hasselbalch equation to connect residues' pKa values (4.8 for COOH and 10.7 for $NH_3$) to pH, we believe cases 1 and 2 to approximate pH 7 and 5, respectively. Our treatment (case 2) of the partial ionization of the COOH group is a mean-field one; an alternative is to probabilistically charge residues and average over many simulations with different realizations of this disorder.

Our Monte Carlo simulations (FIGS. 13c and 13d) consisted of three types of proposed move: 1) swaps of two randomly chosen peptoids; 2) left-right direction reversals of randomly-chosen individual peptoids; and 3) translations in either direction of a randomly-chosen row of the monolayer (we allowed rows to move only by integer multiples of the inter-charge separation, modeling the scenario in which local order is strongly dictated by molecules' hydrophobic groups). To preserve detailed balance (and hence microscopic reversibility), each move was accepted with certainty if the energy of the system decreased, and with probability exp $(-\Delta E/k_B T)$ otherwise. Here $\Delta E$ is the energy change following the proposed move. In this way we allowed the monolayer fragment treated in our simulation to relax to thermal equilibrium. This procedure is not designed to mimic a realistic dynamics, but is instead designed to determine the configurations that molecules might adopt if they self-assemble close to thermal equilibrium.

REFERENCES CITED

1. Bryson, J. W.; Betz, S. F.; Lu, H. S.; Suich, D. J.; Zhou, H. X. X.; Oneil, K. T.; Degrado, W. F. Science 1995, 270, 935-941.
2. Guzzo, A. V. Biophysical Journal 1965, 5, 809-822.
3. Zhang, Y. Current Opinion in Structural Biology 2008, 18, 342-348.
4. Bonneau, R.; Baker, D. Annual Review of Biophysics and Biomolecular Structure 2001, 30, 173-189.
5. MacKerell, J. A. D. In Annual Reports in Computational Chemistry; David, C. S., Ed.; Elsevier, 2005, p 91-102.
6. Butterfoss, G. L.; Renfrew, P. D.; Kuhlman, B.; Kirshenbaum, K.; Bonneau, R. Journal of the American Chemical Society 2009, 131, 16798-16807.
7. Zuckermann, R. N.; Kerr, J. M.; Kent, S. B. H.; Moos, W. H. Journal of the American Chemical Society 1992, 114, 10646-10647.
8. Hill, D. J.; Mio, M. J.; Prince, R. B.; Hughes, T. S.; Moore, J. S. Chemical Reviews 2001, 101, 3893-4011.
9. Cheng, R. P.; Gellman, S. H.; DeGrado, W. F. Chemical Reviews 2001, 101, 3219-3232.
10. DeGrado, W. F.; Schneider, J. P.; Hamuro, Y. Journal of Peptide Research 1999, 54, 206-217.
11. Cheng, R. P.; DeGrado, W. F. Journal of the American Chemical Society 2002, 124, 11564-11565.
12. Lelais, G.; Seebach, D.; Jaun, B.; Mathad, R. I.; Flogel, O.; Rossi, F.; Campo, M.; Wortmann, A. Helvetica Chimica Acta 2006, 89, 361-403.
13. Bruckner, A. M.; Chakraborty, P.; Gellman, S. H.; Diederichsen, U. Angewandte Chemie-International Edition 2003, 42, 4395-4399.
14. Qiu, J. X.; Petersson, E. J.; Matthews, E. E.; Schepartz, A. Journal of the American Chemical Society 2006, 128, 11338-11339.
15. Daniels, D. S.; Petersson, E. J.; Qiu, J. X.; Schepartz, A. Journal of the American Chemical Society 2007, 129, 1532.
16. Petersson, E. J.; Schepartz, A. Journal of the American Chemical Society 2008, 130, 821-823.
17. Armand, P.; Kirshenbaum, K.; Goldsmith, R. A.; Farr-Jones, S.; Barron, A. E.; Truong, K. T. V.; Dill, K. A.; Mierke, D. F.; Cohen, F. E.; Zuckermann, R. N.; Bradley, E. K. Proceedings of the National Academy of Sciences of the United States of America 1998, 95, 4309-4314.
18. Kirshenbaum, K.; Barron, A. E.; Goldsmith, R. A.; Armand, P.; Bradley, E. K.; Truong, K. T. V.; Dill, K. A.; Cohen, F. E.; Zuckermann, R. N. Proceedings of the National Academy of Sciences of the United States of America 1998, 95, 4303-4308.
19. Armand, P.; Kirshenbaum, K.; Falicov, A.; Jr., R. L. D.; Dill, K. A.; Zuckermann, R. N.; Cohen, F. E. Folding and Design 1997, 2, 369-375.
20. Sanborn, T. J.; Wu, C. W.; Zuckermann, R. N.; Barron, A. E. Biopolymers 2002, 63, 12-20.
21. Wu, C. W.; Sanborn, T. J.; Huang, K.; Zuckermann, R. N.; Barron, A. E. Journal of the American Chemical Society 2001, 123, 6778-6784.
22. Wu, C. W.; Sanborn, T. J.; Zuckermann, R. N.; Barron, A. E. Journal of the American Chemical Society 2001, 123, 2958-2963.

23. Burkoth, T. S.; Beausoleil, E.; Kaur, S.; Tang, D. Z.; Cohen, F. E.; Zuckermann, R. N. Chemistry & Biology 2002, 9, 647-654.

24. Lee, B. C.; Zuckermann, R. N.; Dill, K. A. Journal of the American Chemical Society 2005, 127, 10999-11009.

25. Lee, B. C.; Chu, T. K.; Dill, K. A.; Zuckermann, R. N. Journal of the American Chemical Society 2008, 130, 8847-8855.

26. Xiong, H.; Buckwalter, B. L.; Shieh, H. M.; Hecht, M. H. Proceedings of the National Academy of Sciences of the United States of America 1995, 92, 6349-6353.

27. Nam, K. T.; Shelby, S. A.; Choi, P. H.; Marciel, A. B.; Chen, R.; Tan, L.; Chu, T. K.; Mesch, R. A.; Lee, B. C.; Connolly, M. D.; Kisielowski, C.; Zuckermann, R. N. Nature Materials 2010, 9, 454-460.

28. Faul, C. F. J.; Antonietti, M. Advanced Materials 2003, 15, 673-683.

29. Hammond, P. T. Advanced Materials 2004, 16, 1271-1293.

30. Caplan, M. R.; Moore, P. N.; Zhang, S. G.; Kamm, R. D.; Lauffenburger, D. A. Biomacromolecules 2000, 1, 627-631.

31. Bowerman, C. J.; Ryan, D. M.; Nissan, D. A.; Nilsson, B. L. Molecular Biosystems 2009, 5, 1058-1069.

32. Jackson, J.; Fox, R. American Journal of Physics 1999, 67, 841.

33. Figliozzi, G. M.; Goldsmith, R.; Ng, S.; Banville, S. C.; Zuckermann, R. N. Methods in Enzymology 1996, 267, 437-447.

The above cited references are hereby each individually incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A peptoid based two-dimensional sheet comprising a plurality of peptoid oligomers having the structure:

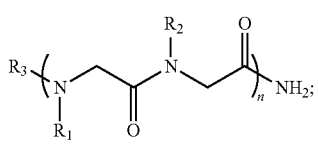

(I)

wherein $R_1$ is a hydrophilic or polar side-chain and $R_2$ is a hydrophobic or apolar side-chain, or $R_2$ is a hydrophilic or polar side-chain and $R_1$ is a hydrophobic or apolar side-chain, $R_3$ is H or a capping group, and n is an integer equal to or greater than 4; wherein the structure within the brackets is a monomer subunit and each monomer subunits can be identical or distinct from each other; or

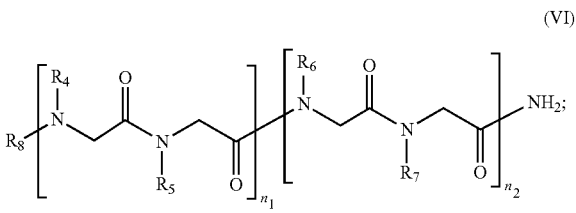

(VI)

wherein (a) $R_4$ is a hydrophilic or polar side-chain and $R_5$ is a hydrophobic or apolar side-chain, and $R_6$ is a negative-charged hydrophilic or polar hydrophilic side-chain and $R_7$ is a hydrophobic or apolar side-chain, wherein $R_4$ and $R_6$ are positive-charged or basic and negative-charged or acidic side-chains, respectively, or vice versa, or (b) $R_5$ is a hydrophilic or polar side-chain and $R_4$ is a hydrophobic or apolar side-chain, and $R_7$ is a negative-charged hydrophilic or polar hydrophilic side-chain and $R_6$ is a hydrophobic or apolar side-chain, wherein $R_5$ and $R_7$ are positive-charged or basic and negative-charged or acidic side-chains, respectively, or vice versa; $R_8$ is H or a capping group; $n_1$ and $n_2$ are an integer equal to or greater than 2; and, $n_1$ and $n_2$ are equal to each other; wherein the plurality of peptoid oligomers are self-assembled with each other into the two-dimensional sheet.

2. The peptoid based two-dimensional sheet of claim 1, wherein each side-chain is independently $R_a$, $-OR_a$, $-NR_aR_b$, $-SO_{1,2,3,4}R_a$, $-C(O)R_a$, $-C(O)OR_a$, $-OC(O)R_a$, $-OC(O)OR_a$, $-NR_bC(O)R_a$, $-C(O)NR_aR_b$, $-OC(O)NR_aR_b$, $NR_c C(O)NR_aR_b$, $-NR_b C(O)OR_a$, $-R_a O-R_b$, $-R_a-NR_bR_c$, $-SO_3$, $-SO_4$, $-SO_2NH-R_a$, $-R_a-S-R_b$, $-R_a-S(O)-R_b$, $-R_a-S(O)_2-R_b$, $-OR_a-O-R_b$, $-NR_aR_b-O-R_c$, $-SO_{1,2,3,4}R_a-O-R_b$, $-C(O)R_a-O-R_b$, $-C(O)OR_a-O-R_b$, $-OC(O)R_a-O-R_b$, $-OC(O)OR_a-O-R_b$, $-NR_bC(O)R_a-O-R_c$, $-C(O)NR_aR_b-O-R_c$, $-OC(O)NR_aR_b-O-R_c$, $-NR_cC(O)NR_aR_b-O-R_d$, $-NR_bC(O)OR_a-O-R_c$, $-OR_a-S-R_b$, $-NR_aR_b-S-R_c$, $-SO_{1,2,3,4}R_{a-S-Rb}$, $-C(O)R_a-S-R_b$, $-C(O)OR_a-S-R_b$, $-OC(O)R_a-S-R_b$, $-OC(O)OR_a-S-R_b$, $-NR_b C(O)R_a-S-R_c$, $-C(O)NR_aR_b-S-R_c$, $-OC(O)NR_aR_b-S-R_c$, $-NR_c C(O)NR_aR_b-S-R_d$, $-NR_bC(O)OR_a-S-R_c$, $-OR_a-NR_bR_d$, $-NR_aR_b-NR_cR_d$, $-SO_{1,2,3,4}R_a-NR_bR_d$, $-C(O)R_a-NR_bR_d$, $-C(O)OR_a-NR_bR_d$, $-OC(O)R_a-N-R_bR_d$, $-OC(O)OR_a-NR_bR_d$, $-NR_bC(O)R_a-NR_cR_d$, $-C(O)NR_aR_b-NR_cR_d$, $-OC(O)NR_aR_b-NR_cR_d$, $-NR_c C(O)NR_aR_b-NHR_d$, $-NR_bC(O)OR_a-NR_cR_d$, $-PO_3$, $-PO_4$, $-PO_2-R_a$, $-R_a-PO_3$, $-R_a-PO_4$, $-R_a-PO_2-R_b$; wherein $R_a$, $R_b$, $R_c$, and $R_d$ are each independently H, alkyl, alkenyl, alkynyl, aryl, aralkyl, aralkenyl, or aralkynyl; wherein $R_a$, $R_b$, $R_c$ and $R_d$ is each independently substituted with 0-6 halo, $NO_2$, $-OH$, lower alkyl, $-SH$, $-SO_3$, $-NH_2$, $-C(O)OH$, lower acyl, lower acyloxy, lower alkylamino, lower dialkylamino, trihalomethyl, $-CN$, lower alkylthio, lower alkylsufinyl, or lower alkylsulfonyl; wherein the number of carbon atoms in the longest carbon chain of $R_a$, $R_b$, $R_c$, and $R_d$ is equal to or less than eighteen; and the proviso than when the side-chain is $R_a$, $R_a$ comprises at least two carbon atoms.

3. The peptoid based two-dimensional sheet of claim 1, wherein one hydrophilic or polar side-chain out of a plurality of hydrophilic or polar side-chains within each oligomer comprises a functional group.

4. The peptoid based two-dimensional sheet of claim 3, wherein the functional group is a dye or a point of attachment to link to another molecule of interest.

5. The peptoid based two-dimensional sheet of claim 1, wherein the apolar side-chain is an aralkyl.

6. The peptoid based two-dimensional sheet of claim 5, wherein the aralkyl is —$CH_2$—$CH_2$—$C_6H_5$.

7. The peptoid based two-dimensional sheet of claim 1, wherein the polar side-chain is a carboxylated alkyl or an aminated alkyl.

8. The peptoid based two-dimensional sheet of claim 7, wherein the carboxylated alkyl is —$CH_2$—$CH_2$—COOH.

9. The peptoid based two-dimensional sheet of claim 7, wherein the aminated alkyl is —$CH_2$—$CH_2$—$NH_2$.

10. The peptoid based two-dimensional sheet of claim 4, wherein the dye is a fluorescent dye.

11. The peptoid based two-dimensional sheet of claim 2, wherein the capping group is $R_a$ and the capping group does not prevent the peptoid oligomer from self-assembling into a two-dimensional sheet with other peptoid oligomers.

12. The peptoid based two-dimensional sheet of claim 2, wherein each hydrophilic or polar side-chain is a side-chain that comprises one or more —$OCH_3$, diol, triol, sugar, —$PO_3$, —$PO_4$, —$PO_2$—$R_b$, —$SO_3$, —$SO_4$, or —$SO_2NH$—$R_b$, one or more ionic charge, is capable of hydrogen-bonding, and/or has a net log P value that is less than 0.

13. The peptoid based two-dimensional sheet of claim 1, wherein each hydrophilic side-chain is —R,—X, wherein X is —OH, —C(O)H, —C(O)OH, —SH, —$NH_2$, or —C(O)—$NH_2$, wherein $R_a$ is an alkyl, alkenyl, alkynyl, aryl, aralkyl, aralkenyl, or aralkynyl, wherein the number of carbon atoms in the longest carbon chain of $R_a$ is equal to or less than eighteen; and $R_a$ comprises at least two carbon atoms.

14. The peptoid based two-dimensional sheet of claim 1, wherein each hydrophobic or apolar side-chain is a side-chain that does not comprises an ionic charge, is not capable of hydrogen-bonding, or has a net log P value that is equal to or more than 0.5.

15. The peptoid based two-dimensional sheet of claim 14, wherein each hydrophobic side-chain has a net log P value that is equal to or more than 1 or 2.

16. The peptoid based two-dimensional sheet of claim 1, wherein each hydrophobic side-chain is —$R_a$—Y, wherein Y is a lower alkyl, a benzene, or a benzene substituted with any lower alkyl, wherein $R_a$ is an alkyl, alkenyl, alkynyl, aryl, aralkyl, aralkenyl, or aralkynyl, wherein the number of carbon atoms in the longest carbon chain of $R_a$ is equal to or less than eighteen; and $R_a$ comprises at least two carbon atoms.

17. The peptoid based two-dimensional sheet of claim 1, wherein the peptoid oligomer comprises 10 or more monomer subunits.

* * * * *